US012226436B2

(12) United States Patent
Kajita et al.

(10) Patent No.: US 12,226,436 B2
(45) Date of Patent: Feb. 18, 2025

(54) TRANSPLANT MATERIAL FOR TREATMENT OF HEART DISEASE

(71) Applicant: ROHTO PHARMACEUTICAL CO., LTD, Osaka (JP)

(72) Inventors: Daisuke Kajita, Suita (JP); Satsuki Fukushima, Suita (JP); Shigeru Miyagawa, Suita (JP); Yoshiki Sawa, Suita (JP)

(73) Assignee: ROHTO PHARMACEUTICAL CO., LTD., Osaka (JP)

( * ) Notice: Subject to any disclaimer, the term of this patent is extended or adjusted under 35 U.S.C. 154(b) by 824 days.

(21) Appl. No.: 16/071,123

(22) PCT Filed: Jan. 18, 2017

(86) PCT No.: PCT/JP2017/001538
§ 371 (c)(1),
(2) Date: Jul. 19, 2018

(87) PCT Pub. No.: WO2017/126549
PCT Pub. Date: Jul. 27, 2017

(65) Prior Publication Data
US 2021/0187031 A1 Jun. 24, 2021

(30) Foreign Application Priority Data
Jan. 19, 2016 (JP) ................. 2016-008096

(51) Int. Cl.
*A61K 35/28* (2015.01)
*A61K 35/35* (2015.01)
*A61K 35/51* (2015.01)
*A61K 35/545* (2015.01)

(52) U.S. Cl.
CPC .............. *A61K 35/28* (2013.01); *A61K 35/35* (2013.01); *A61K 35/51* (2013.01); *A61K 35/545* (2013.01)

(58) Field of Classification Search
CPC ...... A61K 35/28; A61K 35/51; A61K 35/545; A61K 35/35
See application file for complete search history.

(56) References Cited

U.S. PATENT DOCUMENTS

| 2009/0053277 A1 | 2/2009 | Nagaya et al. |
| 2010/0009399 A1 | 1/2010 | Sartipy et al. |
| 2010/0151574 A1 | 6/2010 | Matsuyama et al. |
| 2012/0308533 A1 | 12/2012 | Imanishi et al. |
| 2015/0291934 A1 | 10/2015 | Matsuyama et al. |

FOREIGN PATENT DOCUMENTS

| CN | 101443023 A | 5/2009 |
| CN | 101517069 A | 8/2009 |
| CN | 104350146 A | 2/2015 |
| EP | 2465923 A2 | 6/2012 |
| JP | 2009-542237 A | 12/2009 |
| JP | 5103626 B2 | 12/2012 |
| JP | 5661048 B2 | 1/2015 |
| WO | 2005/047491 A2 | 5/2005 |
| WO | 2006/127007 A2 | 11/2006 |
| WO | 2008/153179 A1 | 12/2008 |
| WO | 2013/162057 A1 | 10/2013 |

OTHER PUBLICATIONS

Vickaryous MK, Hall BK. Human cell type diversity, evolution, development, and classification with special reference to cells derived from the neural crest. Biol Rev Camb Philos Soc. Aug. 2006;81(3):425-55. (Year: 2006).*
Mora C, Tittensor DP, Adl S, Simpson AG, Worm B. How many species are there on Earth and in the ocean? PLoS Biol. Aug. 2011;9(8):e1001127. (Year: 2011).*
Buckley CD, Rainger GE, Bradfield PF, Nash GB, Simmons DL. Cell adhesion: more than just glue (review). Mol Membr Biol. Oct.-Dec. 1998;15(4):167-76 (Year: 1998).*
Chen A, Moy VT. Cross-linking of cell surface receptors enhances cooperativity of molecular adhesion. Biophys J. Jun. 2000;78(6):2814-20. (Year: 2000).*
Yu, X., Liu, Z., Janzen, J. et al. Polyvalent choline phosphate as a universal biomembrane adhesive. Nature Mater 11, 468-476 (2012). (Year: 2012).*
Fergal J. O'Brien. Biomaterials & scaffolds for tissue engineering. Materials Today. vol. 14, Issue 3, 2011, pp. 88-95, (Year: 2011).*
Lin Z, Pu WT. Strategies for cardiac regeneration and repair. Sci Transl Med. 2014;6(239):239rv1. (Year: 2014).*
Jackson MR. Fibrin sealants in surgical practice: An overview. Am J Surg. Aug. 2001;182(2 Suppl):1S-7S. (Year: 2001).*
Christman KL, Lee RJ. Biomaterials for the treatment of myocardial infarction. J Am Coll Cardiol. Sep. 5, 2006;48(5):907-13. (Year: 2006).*
Ankrum JA, Ong JF, Karp JM. Mesenchymal stem cells: immune evasive, not immune privileged. Nat Biotechnol. Mar. 2014;32(3):252-60. (Year: 2014).*
Buja LM, Vela D. Current status of the role of stem cells in myocardial biology and repair. Cardiovasc Pathol. Sep.-Oct. 2011;20(5):297-301. (Year: 2011).*
Li J, Ezzelarab MB, Cooper DK. Do mesenchymal stem cells function across species barriers? Relevance for xenotransplantation. Xenotransplantation. 2012;19(5):273-285. (Year: 2012).*
Kean TJ, Lin P, Caplan AI, Dennis JE. MSCs: Delivery Routes and Engraftment, Cell-Targeting Strategies, and Immune Modulation. Stem Cells Int. 2013;2013:732742. (Year: 2013).*
Huang JV, Greyson CR, Schwartz GG. PPAR-γ as a therapeutic target in cardiovascular disease: evidence and uncertainty. J Lipid Res. Sep. 2012;53(9):1738-54. (Year: 2012).*

(Continued)

*Primary Examiner* — Anoop K Singh
*Assistant Examiner* — David A Montanari
(74) *Attorney, Agent, or Firm* — Sughrue Mion, PLLC

(57) ABSTRACT

It has been found that a cell cluster obtained by causing just isolated cells to adhere to each other secretes adiponectin after transplantation to the heart, and thereby has an excellent therapeutic effect on heart disease.

2 Claims, 38 Drawing Sheets

(56) References Cited

OTHER PUBLICATIONS

Panfilov IA, de Jong R, Takashima S, Duckers HJ. Clinical study using adipose-derived mesenchymal-like stem cells in acute myocardial infarction and heart failure. Methods Mol Biol. 2013;1036:207-12. (Year: 2013).*

Cai L, Johnstone BH, Cook TG, Tan J, Fishbein MC, Chen PS, March K. IFATS collection: Human adipose tissue-derived stem cells induce angiogenesis and nerve sprouting following myocardial infarction, in conjunction with potent preservation of cardiac function. Stem Cells. Jan. 2009;27(1):230-7. (Year: 2009).*

Tsuji W, Rubin JP, Marra KG. Adipose-derived stem cells: Implications in tissue regeneration. World J Stem Cells. Jul. 2, 20146;6(3):312-21. (Year: 2014).*

Tissell-Solutions for sealant. Package insert. Baxter. 2013. Obtained from: https://mri.cts-mrp.eu/Human/Downloads/AT_H_0317 002_FinalPI_1of2.pdf (Year: 2013).*

Rojas et al. (2015, Tissue Engineering, vol. 21(13/14), pp. 1991-2000) (Year: 2015).*

Zhang et al. (2007, Chin. Med. J., vol. 120(4), pp. 300-307) (Year: 2007).*

Tran et al. (2013, Cell Tissue Bank, vol. 14, pp. 97-106). (Year: 2013).*

Communication, dated Dec. 22, 2020, issued by the State Intellectual Property Office of People's Republic of China in counterpart application No. 201780006848.7.

Communication, dated Jul. 12, 2019, from the European Patent Office in application No. 17741426.5.

Frese, L., et al., "Adipose Derived Tissue Engineered Heart Valve", Journal of Tissue Science & Engineering, vol. 6, Issue 3, 2015, pp. 1-9.

Wu, X., et al., "Fibrin glue as the cell-delivery vehicle for mesenchymal stromal cells in regenerative medicine", Cytotherapy, vol. 14, No. 5, 2012, pp. 555-562 (8 pages).

Li, Y., et al., "Fibrin Gel as an Injectable Biodegradable Scaffold and Cell Carrier for Tissue Engineering", The Scientific World Journal, vol. 2015, 2015, pp. 1-10.

Melhem, M., et al., "A Hydrogel Construct and Fibrin-based Glue Approach to Deliver Therapeutics in a Murine Myocardial Infarction Model", Journal of Visualized Experiments, No. 100, 2015, pp. 1-6.

Christman, K., et al., "Fibrin Glue Alone and Skeletal Myoblasts in a Fibrin Scaffold Preserve Cardiac Function after Myocardial Infarction", Tissue Engineering, vol. 10, Nos. 3-4, 2004, pp. 403-409 (7 pages).

Mori, D., et al., "Abstract 15487: Building New Cellular Therapy for Heart Failure; Combined Strategy Using Adjuvant Drug and Somatic Stem Cells for Enhancement in Cytokine Paracrine Effects", Circulation, 2016, pp. 1-5.

Kosaka, M., et al., "Adipose-Derived Regenerative Cells Promote Tendon-Bone Healing in a Rabbit Model", Arthroscopy: The Journal of Arthroscopic and Related Surgery, vol. 32, No. 5, 2016, pp. 851-859 (9 pages).

Mizushima, T., et al., "A clinical trial of autologous adipose-derived regenerative cell transplantation for a postoperative enterocutaneous fistula", Surgery Today, vol. 46, No. 7, 2015, pp. 835-842 (8 pages).

Zhang, X., et al., "Preservation of the cardiac function in infarcted rat hearts by the transplantation of adipose-derived stem cells with injectable fibrin scaffolds", Experimental Biology and Medicine, vol. 235, No. 12, 2010, pp. 1505-1515 (11 pages).

Mori, D., et al., "Abstract 18638: Combination Therapy With Adipose Tissue-derived Regenerative Cells and Ppar Gamma Agonist Enhance the Regenerative Capacity in the Failing Heart With Ischemic Cardiomyopathy Through the Activated M2-polarized Macrophage", Circulation, 2017, 5 pages.

Satsuki Fukushima, et al., "Choice of cell-delivery route for successful cell transplantation therapy for the heart", Future Cardiol, 2013, pp. 215-227, vol. 9, No. 2.

Kalon K.L. Ho, MD; et al., "Survival After the Onset of Congestive Heart Failure in Framingham Heart Study Subjects", Circulation, Jul. 1993, pp. 107-115, vol. 88, No. 1.

Thomas J. Ryan, et al., "1999 Update: ACC/AHA Guidelines for the Management of Patients With Acute Myocardial Infarction", Journal of the American College of Cardiology, Sep. 1999, pp. 890-911, vol. 34, No. 3.

Corin WJ, et al., "Dynamic cardiomyoplasty acutely impairs left ventricular diastolic function." J. Thorac Cardiovasc Surg., 1992, 1 page, vol. 104, No. 6: 1662-71.

John M. Kratz, MD, et al., "The relation between latissimus dorsi skeletal muscle structure and contractile function after cardiomyoplasty", The Journal of Thoracic and Cardiovascular Surgery, Mar. 1994, pp. 868-878, vol. 107, Issue 3.

A. Carpentier, et al., "Myocardial Substitution With A Stimulated Skeletal Muscle: First Successful Clinical Case", The Lancet, Jun. 1, 1985, p. 1267, vol. 8840.

Albert A. Hagege, et al., "Preliminary report: follow-up after dynamic cardiomyoplasty", The Lancet, May 12, 1990, pp. 1122-1124, vol. 335.

Alexis Carrel, "Heterotransplantation of Blood Vessels Preserved In Cold Storage", J. Exp Med., Mar. 14, 1907, p. 226-228, vol. 9.

Alexis Carrel, "Ultimate Results of Aortic Transplantations", J. Exp Med., Apr. 1, 1912, pp. 389-392, vol. 9.

Roy Y. Calne, "Organ Transplantation Between Widely Disparate Species", Transplantation Proceedings, Dec. 1970, pp. 550-553, vol. 2, No. 4.

Hugh Auchincloss, Jr., "Xenogeneic Transplantation", Transplantation, Jul. 1988, pp. 1-20, vol. 46, No. 1.

Jonathan Leor, et al., "Bioengineered Cardiac Grafts A New Approach to Repair the Infarcted Myocardium?", Circulation, Nov. 2000, pp. III-56-III61, vol. 102.

Ren-Ke Li, MD, et al., "Survival and Function of Bioengineered Cardiac Grafts", Circulation, Nov. 1999, pp. II-63-II-69.

Yoshihiro Yamada, et al., "Cardiac progenitor cells in brown adipose tissue repaired damaged myocardium", Biochemical and Biophysical Research Communications, 2006, pp. 662-670, vol. 342.

Ricardo Sanz-Ruiz, et al., "Adipose Tissue-derived Stem Cells: The Friendly Side of a Classic Cardiovascular Foe", Journal of Cardiovascular Translational Research, Mar. 2008, pp. 55-63, vol. 1, Issue 1.

Rei Shibata, MD, et al., "Adiponectin and Cardiovascular Disease", Circ J. Apr. 2009, pp. 608-614, vol. 73, No. 4.

Philippe Eren, et al., "Adiponectinemia Controls Pro-Angiogenic Cell Therapy", Stem Cells, 2009, pp. 2712-2721, vol. 27, No. 11.

International Search Report for PCT/JP2017/001538 dated Feb. 21, 2017 [PCT/ISA/210].

* cited by examiner

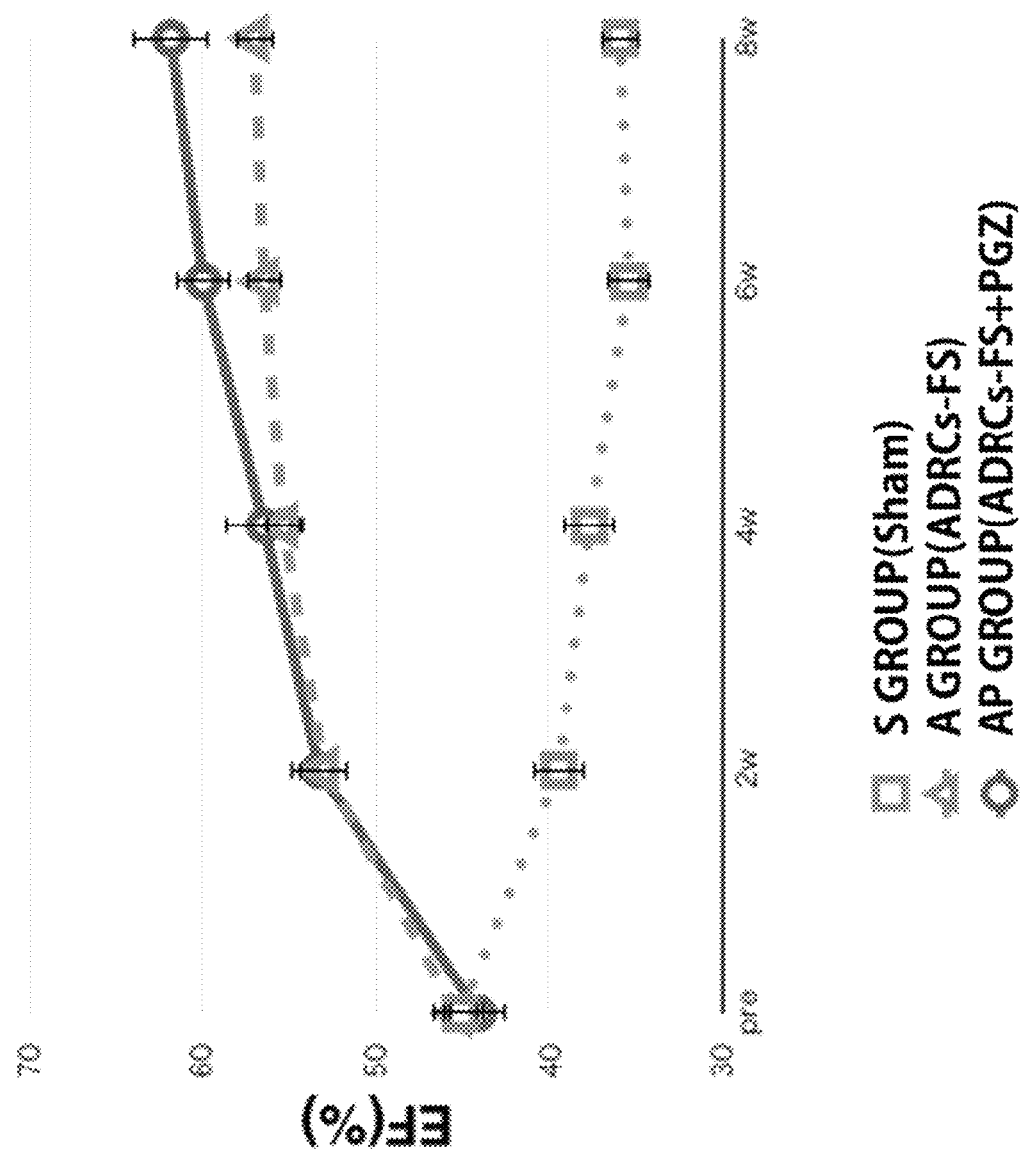

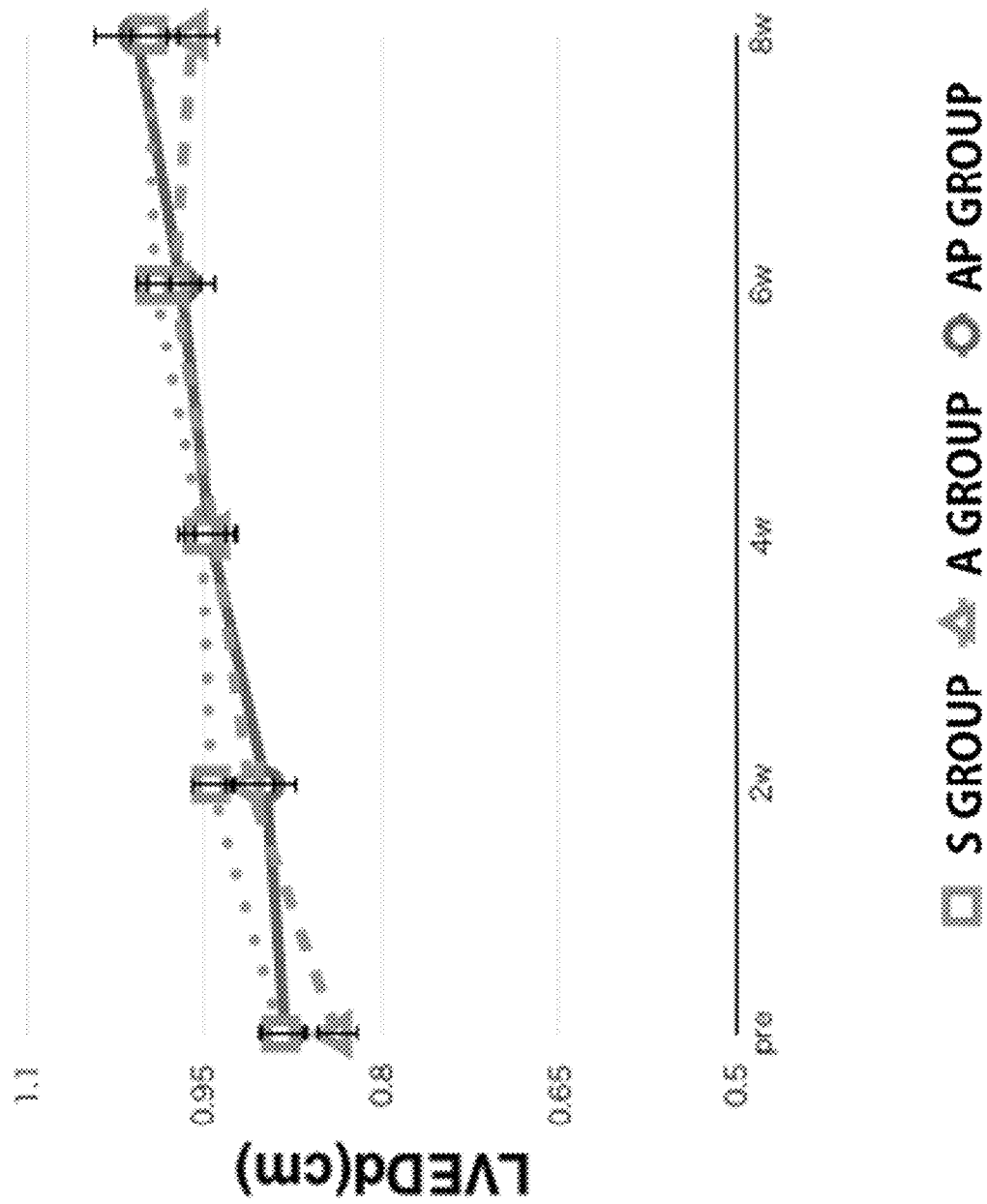

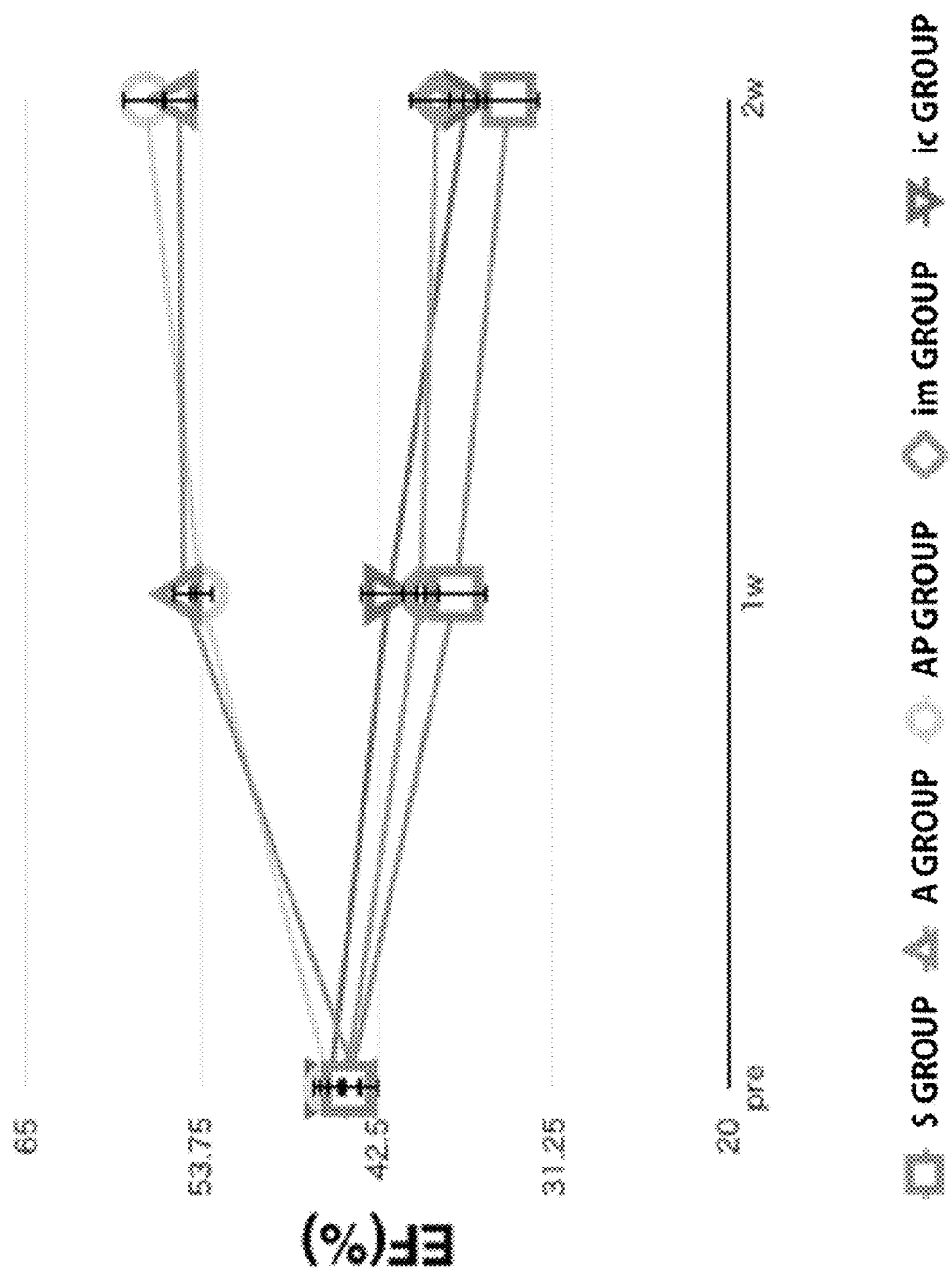

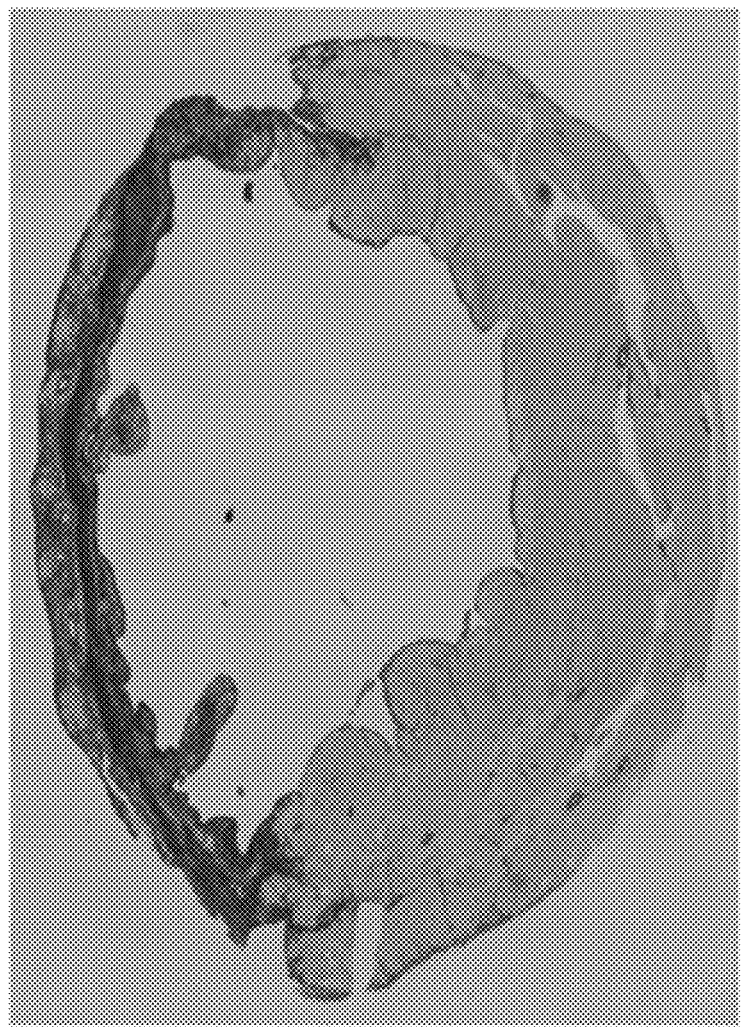
Fig. 5A  S GROUP

A GROUP

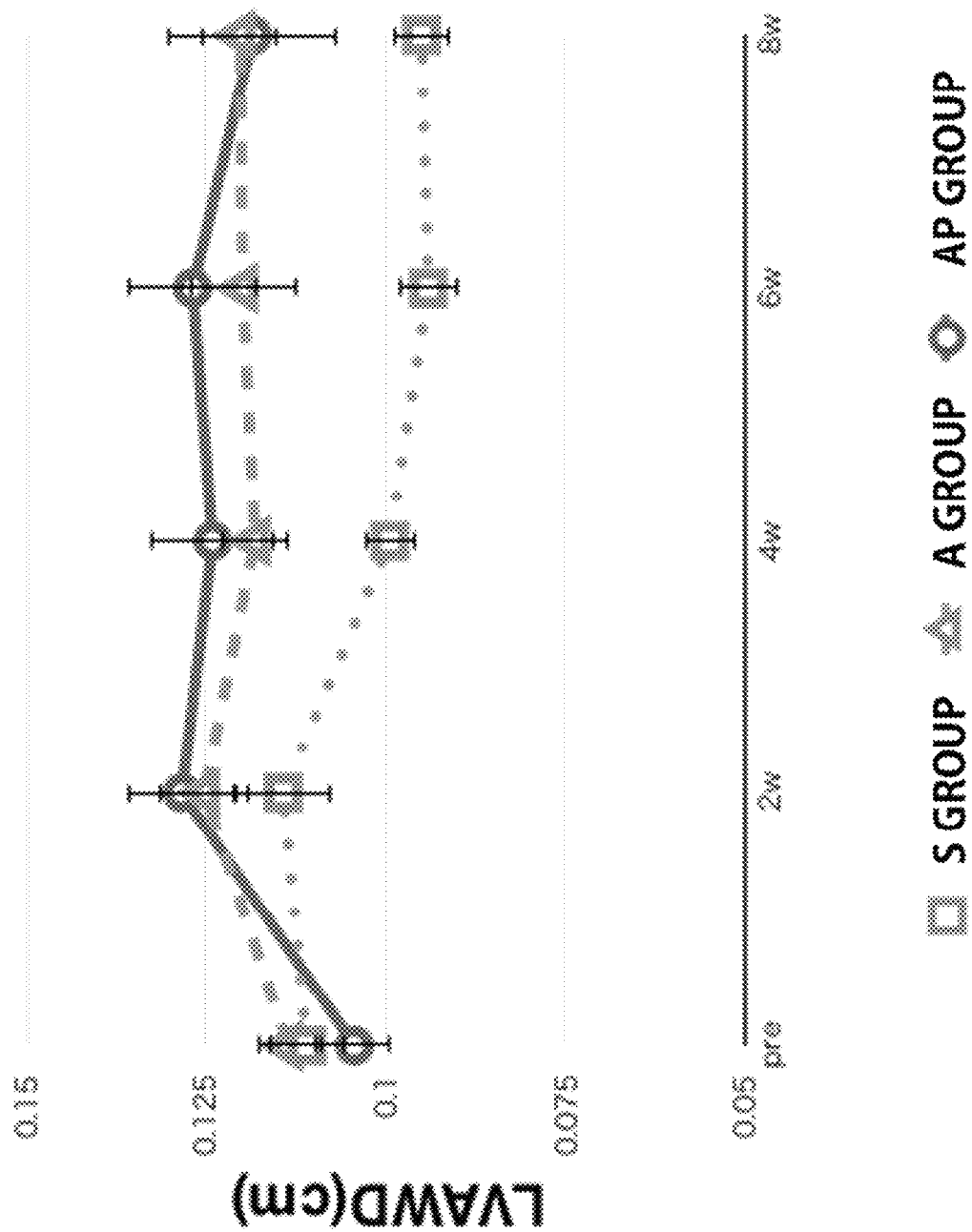

S GROUP

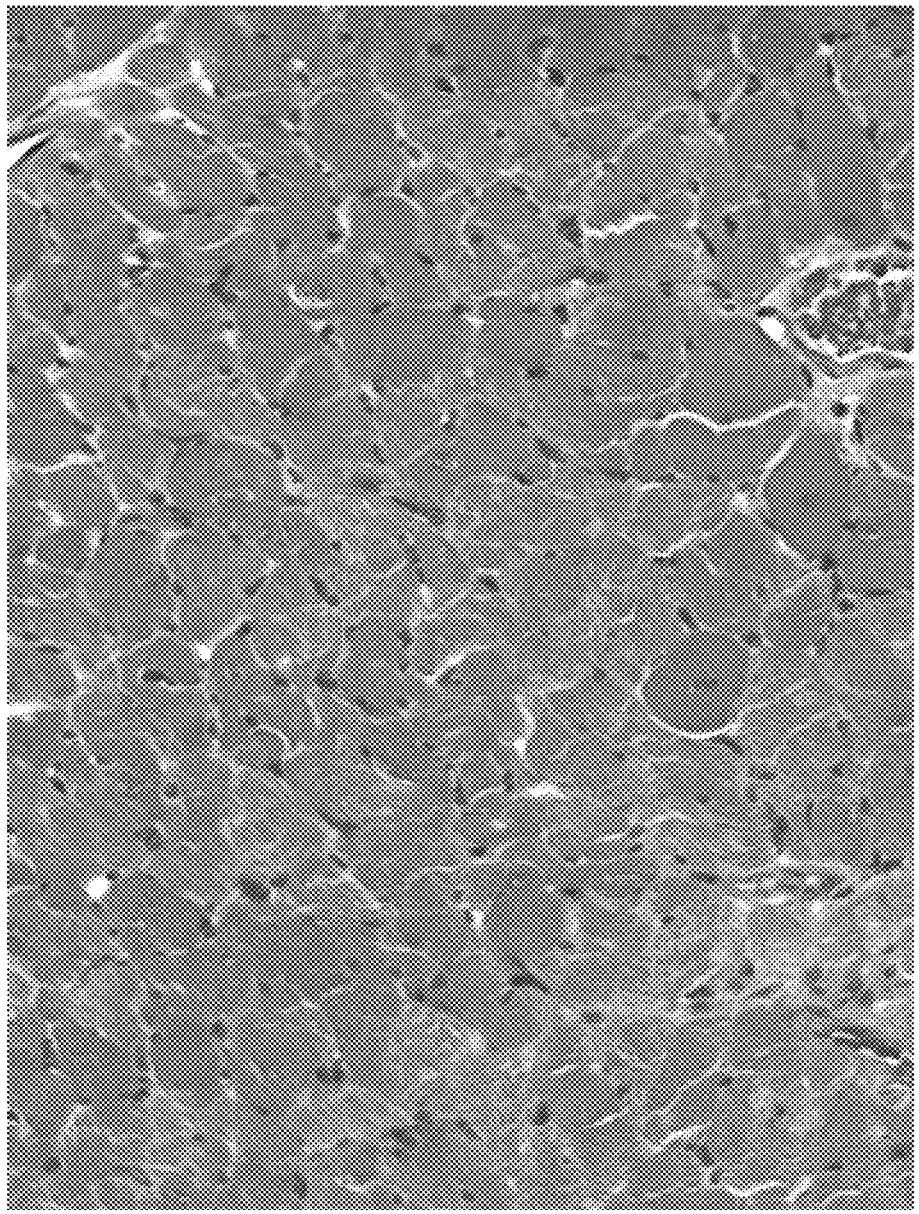
Fig. 6C  AP GROUP

TRANSPLANT MATERIAL FOR TREATMENT OF HEART DISEASE

TECHNICAL FIELD

The present invention relates to a transplant material for treatment of heart disease including a cell cluster obtained by causing isolated cells to adhere to each other with an adhesive agent and a heart disease treatment method using the transplant material.

BACKGROUND ART

Myocardial infarction is an irreversible damage of myocardial cells (NPL 1). Ischemic heart disease accounts for 50% of all cardiovascular mortality causes and is a leading cause of congestive heart failure. If patients diagnosed with congestive heart failure are not ameliorated by treatment, their prognoses are very bad and the 1-year mortality rate is close to 20% (NPL 2). Currently, many of the treatments available to physician s can eliminate the causes of these acute myocardial infarctions, but a time period from infarction onset to reperfusion determines the extent of irreversible myocardial damage (NPL 3). Cardiomyoplasty has been proposed as a surgical method for improving left ventricular (LV) function in patients suffering from congestive heart failure, but the effect on cardiac function and patients' prognoses are not satisfactory (NPLs 4 to 7). Any clinically available drugs and treatments are ineffective in replacing a myocardial scar with functionally contractile tissue, and there is a demand for novel treatment for regenerating normal myocardial cells.

In transplantation of an organ (for example, the heart, a blood vessel, or the like) as a replacement treatment, use of graft tissue such as an allogeneic graft (or an allograft) or a xenograft has been reported to cause immunological rejection (NPLs 8 to 11). For example, transplantation of a cardiac graft biologically manipulated using biodegradable scaffolds has demonstrated minimal benefits in improving the cardiac function, because the cardiac graft hardly engraft to the myocardial layer (NPLs 12 and 13). Meanwhile, transplantation of a whole heart is not the first choice for a heart failure due to donor shortage.

Recently, cell transplantations have attracted attention as treatment methods utilizing biological substances such as iPS cells and mesenchymal stem cells (MSC). These cell transplantations have also been reported that they have the possibility of replacing damaged myocardial tissue and improving the cardiac function. For example, there has been studies on methods for preparing and transplanting adipose-derived cells, in which they are directly administered by intramyocardial injection or intracoronary injection. However, it has been reported that these administration methods cannot obtain sufficient therapeutic effects or even cause serious adverse effects (such as arrhythmia) after the transplantation (PTL 1 and NPLs 14 and 15).

To address this, studies on administration methods other than injections have resulted in development of a method in which a stem cell is cultured on a temperature-responsive culture dish and processed into a sheet, and then the sheet is transplanted onto the cardiac surface. This method can transplant cells without causing serious adverse effects, and has drawn attention as producing the therapeutic effects by the paracrine of the cytokines which are secreted from the transplanted cells and have myocardial protection and angiogenesis effect (PTL 2).

In addition, it has also been reported that adiponectin known as cytokines secreted from adipocytes has a possibility of protecting the cardiomyocyte after injury and suppressing the deterioration of the cardiac function through the effects of anti-apoptosis, anti-inflammation, angiogenesis, anti-fibrosis, and anti-cardiac hypertrophy (NPLs 16 and 17). Furthermore, studies on adipocyte transplantations as a drug delivery system (DDS) have also been done as means for adiponectin administration to target cardiac tissue over a long period of time. As a result, it has been found that the adiponectin secreted from a cell sheet prepared from matured adipocytes differentiated by culture and transplanted onto the cardiac surface can improve the cardiac function over a long period (PTL 3).

However, preparations of these cell sheets for transplantation require much time and efforts and therefore have a problem in using in clinical situation.

CITATION LIST

Patent Literature

[PTL 1] Japanese Patent No. 5210155
[PTL 2] Japanese Patent No. 5103626
[PTL 3] Japanese Patent No. 5661048

Non Patent Literature

[NPL 1] Ho KK et al., Circulation 1993; 88: 107-115
[NPL 2] American Heart Association, Dallas, Tex.: American Heart Association; 2001
[NPL 3] Ryan T J et al., J Am Coll Cardiol 1999; 34: 890-911
[NPL 4] Corin W J et al., J Thorac Cardiovasc Surg 1992; 104: 1662-71
[NPL 5] Kratz J M et al., J Thorac Cardiovasc Surg 1994; 107: 868-78
[NPL 6] Carpentier A, Chachques J C., Lancet. 1985; 8840:1267
[NPL 7] Hagege A A et al., Lancet 1990; 335: 1122-4
[NPL 8] Carrel A, J Exp Med 1907; 9: 226-8
[NPL 9] Carrel A, J Exp Med 1912; 9: 389-92
[NPL 10] Calne R Y, Transplant Proc 1970; 2: 550
[NPL 11] Auchincloss, Transplantation 1988; 46:1
[NPL 12] Leor J et al., Circulation 2000; 102[suppl III] III-56-III-61
[NPL 13] Li R K et al., Circulation 1999; 100[suppl II]: II-63-II-69
[NPL 14] Yamada Y et al., Biochem Biophys Res Commun 2006; 342(2): 662-670
[NPL 15] Sanz-Ruiz R et al., J Cardiovasc Transl Res 2008; 1(1): 55-63
[NPL 16] Shibata R et al., Circ J 2009; 73(4): 608-614
[NPL 17] Eren P et al., Stem Cells 2009; 27(11): 2712-2721

SUMMARY OF INVENTION

Technical Problem

The present invention has been made in view of the aforementioned circumstances and has an object to provide a transplant material which has an excellent therapeutic effect on heart disease and which can be prepared easily within a short period of time. A further object of the present invention is to provide a heart disease treatment method using this transplant material.

Solution to Problem

As a result of intensive studies to solve the above-mentioned problems, the inventor of the present invention found that a cell cluster, obtained in such a way that regenerative cells just isolated from living adipose tissue are caused to adhere to each other without culturing, secretes adiponectin after transplantation to the heart and thereby exerts an excellent therapeutic effect on heart disease. In production of this cell cluster, a cell cluster was able to be easily produced by using fibrinogen as an adhesive material of the cells. In addition, the therapeutic effect was further enhanced by using adipose-derived mesenchymal progenitor cells treated with a PPARγ agonist in the production of the cell cluster.

Conventionally, in the case of a treatment of heart disease with a cell sheet produced from adipocytes or stem cells derived from adipose tissue, culturing of cells over a long period of time has been required before the production of the cell sheet. For example, according to PTL 3, in order to differentiate cells into mature adipocytes, the cells are generally cultured in a prescribed medium for 5 to 10 days before induction of differentiation after seeding, for 36 to 60 hours during the induction of differentiation, and for 5 to 14 days after the induction of differentiation. The cell culturing for periods shorter than the above is said to be unfavorable in practice due to reasons such as one that the obtained cells secrete only a small amount of adiponectin (paragraph 0025).

Meanwhile, a method in PTL 2 produces the therapeutic effect on heart disease by using a cell sheet not containing mature adipocytes but containing mesenchymal stem cells derived from adipose tissue. Also according to this method, collected stem cells are cultured in a prescribed medium generally for several days, and then the cells are subcultured for several generations to produce a cell sheet (paragraphs 0013 and 0014). However, PTL 2 only states that the mesenchymal stem cells in this cell sheet differentiate into cardiomyocyte, vascular endothelial cells, and vascular smooth muscle cells after transplantation to the heart, and does not mention anything about the differentiation into mature adipocytes and the accompanying secretion of adiponectin (paragraphs 0017 and 0018).

Under such circumstances, it is extremely surprising that a cell cluster obtained by causing cells just isolated from living adipose tissue to adhere to each other secreted adiponectin after transplantation into the heart, and demonstrated an excellent therapeutic effect on heart disease.

As described above, the present invention is intended to provide a transplant material which can be prepared easily within a short period of time and has an excellent therapeutic effect on heart disease, and a heart disease treatment method using the transplant material, and more specifically to provide the invention described below.

[1] A transplant material for treating heart disease, the transplant material comprising a cell cluster obtained by causing isolated cells to adhere to each other with an adhesive agent.

[2] The transplant material according to [1], wherein the isolated cells are selected from the group consisting of adipose-derived regenerative cells, bone marrow-derived regenerative cells, umbilical cord-derived regenerative cells, smooth muscle-derived regenerative cells, multipotent stem cells, regenerative cells derived from the multipotent stem cells, vascular endothelial cells, and monocytes.

[3] The transplant material according to [1], wherein the isolated cells are adipose-derived regenerative cells treated with a PPARγ agonist.

[4] The transplant material according to any one of [1] to [3], wherein the isolated cells are cells not cultured.

[5] The transplant material according to any one of [1] to [4], wherein the adhesive agent contains fibrinogen.

[6] A heart disease treatment method comprising covering a cardiac surface of a subject suffering from heart disease with the transplant material according to any one of [1] to [5].

[7] The treatment method according to [6], wherein the subject suffering from the heart disease is a subject from whom cells for the transplant material were collected.

Advantageous Effects of Invention

According to the present invention, the cells just isolated can be processed into a cell cluster, which can be then transplanted. Moreover, the cells can be processed into a cell cluster easily using fibrinogen or the like. Therefore, the time, effort, and cost can be drastically reduced compared with conventional transplantation treatment using a cell sheet.

In addition, the method of the present invention is much safer than the conventional transplantation treatment in which adipose-derived mesenchymal progenitor cells are injected into the coronary artery or the cardiomyocyte, and also achieves superior cardiac function recovery in combination with the secretion of adiponectin.

BRIEF DESCRIPTION OF DRAWINGS

FIG. 1A demonstrates photomicrographs (in vitro evaluation) of an ADRCs cell cluster after culture.

FIG. 1B includes graphs demonstrating a result of measurement of adiponectin (APN), VEGF, HGF, and IL-6 in the culture supernatant of the ADRCs cell cluster by enzyme-linked immunosorbent assay (ELISA method) (in vitro evaluation).

FIG. 1C is a microphotograph (in vitro evaluation) of an ADRCs cell cluster after culture. Spherical ones in the picture are oil droplets.

FIGS. 3A-3D include diagrams demonstrating results of echocardiographic examinations on how transplantation therapy of ADRCs cell clusters to myocardial infarction model rats affects the cardiac function. FIG. 3A is a graph of left ventricular ejection fraction (EF).

FIG. 3B is a graph of left ventricular end-systolic diameter (LVESd).

FIG. 3C is a graph of left ventricular end-diastolic diameter (LVEDd).

FIG. 3D is a graph of survival rate.

FIGS. 4A-4C include diagrams each demonstrating a result of echocardiographic examinations on how transplantation of ADRCs cell clusters, ADRCs intramyocardial injection, and ADRCs intracoronary administration to chronic myocardial infarction model rats affect the cardiac function. FIG. 4A is a graph of left ventricular ejection fraction (EF).

FIG. 4B is a graph of left ventricular end-systolic diameter (LVESd).

FIG. 4C is a graph of left ventricular end-diastolic diameter (LVEDd).

FIGS. 5A-5I include diagrams demonstrating results of examinations on how transplantation therapy of ADRCs cell clusters to myocardial infarction model rats affects the myocardial tissue. FIG. 5A is a photomicrograph demonstrating a Picro-Sirius red stained low magnification image of an S group.

FIG. 5B is a photomicrograph demonstrating a Picro-Sirius red stained low magnification image of an A group.

FIG. 5C is a photomicrograph demonstrating a Picro-Sirius red stained low magnification image of an AP group.

FIG. 5D is a graph demonstrating a result of measurements of the left-ventricular end-diastolic wall thickness (LVAWD) of the S group, the A group, and the AP group.

FIG. 5E is a graph demonstrating a result of measurements of the fibrotic area in the left ventricular cross-sectional area of the S group, the A group, the AP group, an ic group, and an im group.

FIG. 5F is a photomicrograph demonstrating a von Willebrand factor-stained image of the infarct-normal border area of the S group.

FIG. 5G is a photomicrograph demonstrating a von Willebrand factor-stained image of the infarct-normal border area of the A group.

FIG. 5H is a photomicrograph demonstrating a von Willebrand factor-stained image of the infarct-normal border area of the AP group.

FIG. 5I is a graph demonstrating a result of measurements of the capillary density in the infarct-normal border area of the S group, the A group, the AP group, the ic group, and the im group.

FIGS. 6A-6G include pictures demonstrating a result of examination on influences on myocardial tissue of chronic myocardial infarction model rats at week 8 after transplantation therapy of ADRCs cell clusters to the rats. FIG. 6A is a photomicrograph demonstrating a hematoxylin-eosin stained low magnification image of the S group.

FIG. 6B is a photomicrograph demonstrating a hematoxylin-eosin stained low magnification image of the A group.

FIG. 6C is a photomicrograph demonstrating a hematoxylin-eosin stained low magnification image of the AP group.

FIG. 6D is a representative tissue photograph demonstrating a result of Periodic acid-Skiff (PAS) staining of the infarct-normal border area of the S group.

FIG. 6E is a representative tissue photograph demonstrating a result of Periodic acid-Skiff (PAS) staining of the infarct-normal border area of the A group.

FIG. 6F is a representative tissue photograph demonstrating a result of Periodic acid-Skiff (PAS) staining of the infarct-normal border area of the AP group.

FIG. 6G is a graph demonstrating a result of quantification of myocardial cell diameters in the myocardial infarct-normal border area of the experimental groups.

FIG. 7A is a graph demonstrating a result of quantification of the transcription level of Adiponectin (APN) in the infarct area and the infarct-normal border area.

FIG. 7B is a graph demonstrating a result of quantification of the transcription level of Adiponectin receptor 1 (Adipo-R1) in the infarct area and the infarct-normal border area.

FIG. 7C is a graph demonstrating a result of quantification of the transcription level of Adiponectin receptor 2 (Adipo-R2) in the infarct area and the infarct-normal border area.

FIG. 7D is a graph demonstrating a result of quantification of the transcription level of T-cadherin in the infarct area and the infarct-normal border area.

FIG. 7E is a graph demonstrating a result of quantification of the transcription level of vascular endothelial growth factor (VEGF) in the infarct area and the infarct-normal border area.

FIG. 7F is a graph demonstrating a result of quantification of the transcription level of Tumor necrosis factor alpha (TNF-α) in the infarct area and the infarct-normal border area.

FIG. 8A is a photograph of tissue taken one week after transplantation of an ADRCs cell cluster derived from a GFP transgenic LEW/Sea rat to the left ventricle of a LEW/Sea rat, the upper part in the picture is the ADRCs cell cluster, and the lower part in the picture is the heart.

FIG. 8B is a photomicrograph demonstrating a result of immunostaining adiponectin in the tissue taken three weeks after the transplantation of an ADRCs cell cluster derived from a GFP transgenic LEW/Sea rat to the left ventricle of a LEW/Sea rat. Regions with light color indicate adiponectin.

FIG. 8C includes photomicrographs demonstrating a result of left ventricular intramyocardial injection of ADRCs derived from a GFP transgenic LEW/Sea rat.

FIG. 8D includes photomicrographs demonstrating a result of intracoronary administration of ADRCs derived from a GFP transgenic LEW/Sea rat.

Figure 1A:
FIGS. 1A-1C include drawings demonstrating a result of histological examination on a cell cluster composed of adipose-derived regenerative cells (ADRCs) (hereinafter also simply referred to "ADRCs cell cluster").
Figure 1A:
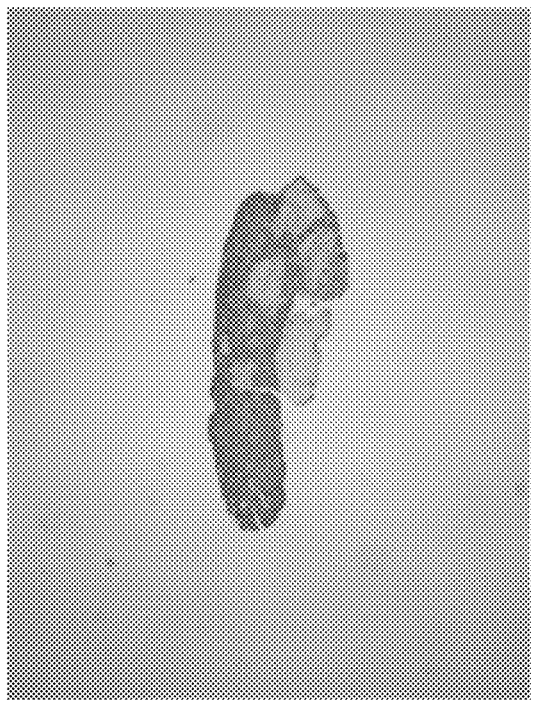

The present invention provides a transplant material for treatment of heart disease, the material comprising a cell cluster obtained by causing isolated cells to adhere to each other with an adhesive agent.

The isolated cells may be any cells not particularly limited as long as the cells have a therapeutic effect on heart disease. Examples thereof include adipose tissue (for example, subcutaneous adipose tissue, greater omentum, and epicardial fat)-derived regenerative cells, bone marrow-derived regenerative cells, umbilical cord-derived regenerative cells, smooth muscle (for example, perivascular smooth muscle)-derived regenerative cells, pluripotent stem cells (for example, iPS cells, ES cells, and Muse cells), and regenerative cells derived therefrom. In addition, it is also possible to use differentiated cells such as vascular endothelial cells and monocytes.

The "regenerative cell" in the present invention means a cell that has an ability to restore the structure and function in an organ or tissue to which the cell is applied. In a preferable embodiment, regenerative cells are of a cell group including mesenchymal stem cells and mesenchymal progenitor cells. Here, the "mesenchymal stem cell" means a stem cell having an ability to differentiate into a mesenchymal cell such as osteoblast, adipocyte, myocyte, or chondrocyte, and the "mesenchymal progenitor cell" means a cell in the process of differentiation from a mesenchymal stem cell to a mesenchymal cell. Then, the "stem cell" means a cell having a self-renewal ability and pluripotency. Whether or not isolated regenerated cells are mesenchymal stem cells or mesenchymal precursor cells can be evaluated by using a predetermined cell surface marker (Lin K et al., Cytotherapy 2008; 10(4): 417-426).

In the present invention, "adipose-derived regenerative cells" are preferably used in particular. The "adipose tissue" is connective tissue composed mainly of adipocytes. The adipose tissue from which regenerative cells are isolated is not particularly limited, but may be subcutaneous adipose tissue, greater omentum, epicardial fat, or the like. The adipose tissue can be collected from a living body, for example, by aspiration from a small incision or by surgical excision.

In a preferred embodiment, a cell cluster obtained by adhesion of cells contains mesenchymal progenitor cells and mesenchymal stem cells in a total amount of at least 1% or more, and preferably 5% or more (for example, 10% or more, 20% or more, 30% or more, 40% or more, or 50% or more). In addition to these cells, the cell cluster may contain, for example, cells mixed in the isolation process, and so on.

The cells can be isolated from the tissue in such a way that the tissue is first fragmented, and the obtained fragments are treated with collagenase, followed by filtration through a filter and then centrifugation. The centrifugation for isolating regenerative cells can be performed under conditions, for example, at 500 to 800 G for 5 to 10 minutes.

In the present invention, isolated cells are caused to adhere to each other to form a cell cluster. The method for causing cells to adhere to each other is not particularly limited, but fibrinogen can be preferably used. The fibrinogen becomes a pasty fibrin polymer when mixed with thrombin, and thus comes to have an ability to bond cells to each other. Therefore, as presented in Examples, cells can be caused to adhere to each other easily by mixing a suspension of cells to which fibrinogen is added with a solution containing thrombin. If the above mixed solution is kept warm, the adhesion can be made faster.

In this way, cells for forming a cell cluster need not be cultured. Thus, it is possible to immediately process the isolated regenerative cells into a cell cluster and to use the cell cluster in transplantation to the heart. Therefore, a process from collection to preparation of a cell cluster can be accomplished within a very short period of time. For example, unlike the present invention, the conventional method using a cell sheet causes the cells to adhere to each other by culture (an adhesive agent is used for the purposes such as reinforcement of the cell sheet) and generally requires a period in the order of several days to several weeks as a period from collection of biological tissue to preparation of a cell sheet. In contrast, the present invention requires only several hours from collection of biological tissue to preparation of a cell sheet, which means achievement of significant time reduction.

In the formation of a cell cluster, it is preferable to use adipose-derived regenerative cells treated with a PPARγ agonist. This allows further enhancement of secretion of adiponectin from the cell cluster after transplantation to the heart. Examples of the PPARγ agonist include, but are not particularly limited to, thiazolidine-based drugs such as pioglitazone. As substances with which adipose-derived cells are treated, there are, besides the above substances, substances that promote induction of differentiation into adipocytes such as insulin and steroid, angiotensin receptor antagonists (ARB), angiotensin converting enzyme inhibitors (ACEi), cytokines such as VEGF and HGF, and so on.

In the case of use for transplantation treatment of heart disease, the cell cluster can be adjusted in size and thickness as appropriate according to a site to which the cell cluster is to be transplanted or the like. Generally preferable cell clusters have a disc shape having a diameter of 5 mm to 5 cm or a square shape having a side of 5 mm to 5 cm, and have a thickness of 0.5 to 2 mm so as to have sufficient strength. In order to obtain such a cell cluster, a suspension can be used which has a cell concentration of $2 \times 10^5$ to $2 \times 10^7$ cells/ml, for example.

The transplant material of the present invention may further contain other elements useful for treating heart disease, as long as it contains the above-mentioned cell cluster. Examples of the other elements include, but are not limited to, a cell cluster or a cell sheet composed of heterologous cells, extracellular matrices, and adhesion factor proteins.

An example of the "heart disease" to be treated by the transplant material of the present invention is, but not limited to, a disease or a disease accompanied by a disorder, the disease selected from the group consisting of heart failure, ischemic heart disease, myocardial infarction, cardiomyopathy, myocarditis, hypertrophic cardiomyopathy, diastolic hypertrophic cardiomyopathy, and dilated cardiomyopathy.

The present invention also provides a heart disease treatment method, the method comprising covering a cardiac surface of a subject suffering from heart disease with the aforementioned transplant material.

The treatment according to the present invention can be applied to human and non-human subjects. Organisms to be treated are not particularly limited as long as they each have a heart as a treatment target, and examples thereof include human, mammals other than human, birds, reptiles, amphibians, and fishes. The mammals other than humans include, but are not limited to, primates such as chimpanzees and monkeys, as well as livestock and companion animals such as cattle, swine, horses, chickens, cats, and dogs.

As the cells from which the transplant material of the present invention is derived, cells compatible with an organism to be treated may be used. However, from the viewpoint of suppression of immune rejection reaction or the like, used are cells derived from the same species, and particularly preferably autologous cells. Therefore, particularly preferably, the transplant material of the present invention is transplanted to a subject from whom the cells were collected.

It should be noted that, even when a rejection reaction is expected in principle, the rejection reaction may be inhibited by using publicly known means such as an immunosuppressive agent. In this way, a range of cells applicable to a particular organism can be expanded.

A site to which the transplant material of the present invention is transplanted is preferably a cardiac surface. In this case, a heart disease can be treated by covering the cardiac surface with the transplant material of the present invention. In the transplantation of the transplant material to the cardiac surface, for example, the transplant material may be attached to a lesion (for example, a myocardial infarction area), and then surgically fixed to the epicardium with a proline needle or fixed to the cardiac surface by fibrin spray. Preferably, the transplant material is placed on the cardiac surface so as to sufficiently cover the boundary between the lesion site (for example, the myocardial infarction site) and the surrounding normal site.

For transplantation, the heart targeted for the transplantation is treated as needed in advance. For example, in the case of an initial surgery, the transplantation is preferably conducted after the blood and moisture on the cardiac surface are wiped off sufficiently. Meanwhile, in the case of a second or following surgery, the transplantation is preferably conducted after the scar tissue on the cardiac surface is removed as quickly as possible.

In the treatment method of the present invention, the treatment with the transplant material of the present invention may be combined with another treatment. For example, for a chronic myocardial infarction, the treatment of the present invention may be combined with coronary artery bypass surgery, percutaneous coronary angioplasty, or left ventricular reconstruction. For an acute myocardial infarction, the treatment of the present invention may be combined with coronary artery bypass surgery or percutaneous coronary angioplasty. In addition, the treatment of the present invention may be combined with valve replacement surgery or pediatric heart surgery.

EXAMPLES

Hereinafter, the present invention is described in more details based on Examples, but the present invention should not be limited to Examples described below.

Example 1

[Materials and Methods]
(1) Preparation for Adipose-Derived Regenerative Cells (ADRCs=Adipose Derived Regenerative Cells)

Adipose tissue was collected from both inguinal regions of a 9 week-old female LEW/Sea rat. The adipose tissue was cut into fine pieces by scissors, and the obtained tissue pieces were suspended in a 0.1% type II collagenase solution and shaken in a 37° C. warm bath for 1 hour. The suspension was filtered through 100 µm and 70 µm mesh filters, followed by centrifugation for 10 minutes at 1800 revolutions per minute. The resultant sediment suspended in a culture medium (10% fetal bovine serum and antibiotic-containing D-MEM) was used as adipose-derived regenerative (mesenchymal progenitor) cells (ADRCs). These include adipose tissue-derived mesenchymal stem cells and progenitor cells.

(2) Production of ADRCs Cell Cluster

Subsequent to the extraction of the ADRCs from the adipose tissue, cell clusters each containing $5 \times 10^6$ ADRCs were produced immediately. A solution A was prepared by adding 60 µl of fibrinogen to 140 µl of the ADRCs cell suspension, whereas a solution B was prepared by adding 30 ml of thrombin to 170 µl of a culture medium (10% fetal bovine serum and antibiotic-containing D-MEM), followed by thorough mixing. Then, the solution A was first dropped on a culture dish, the solution B was added to the dropped solution A, and the obtained mixture was formed into a shape suitable for transplantation, and then was kept warm in a humid environment at 37° C. in a 5% carbon dioxide atmosphere for 5 to 10 minutes to cause the cells to adhere to each other to produce an ADRCs cell cluster. After the production of the ADRCs cell cluster, the cluster was promptly transplanted to an infarct site.

(3) Measurement of Secretion Levels of Cytokines Such as Adiponectin by ADRCs Cell Cluster The supernatant after the ADRCs cell cluster was cultured for 24, 48, 72, 96, 120, and 144 hours was collected, and the secretion levels of adiponectin, VEGF, HGF, and IL-6 in the supernatant were measured by enzyme-linked immunosorbent assay (ELISA).

(4) Histological Examination of ADRCs Cell Cluster

Frozen sections of the ADRCs cell cluster were prepared, fixed with 4% paraformaldehyde, and then subjected to Oil Red O staining and adiponectin immunostaining.

5) Production of Cardiac Insufficiency Model and Transplantation of ADRCs Cell Cluster A myocardial infarction model was prepared using a 7-week old female LEW/Sea rat by a ligation at the anterior descending branch of the left coronary artery. With a general anesthesia given by inhalation anesthesia of isoflurane under artificial respiration (1.5% isoflurane, ventilation volume 4 ml, 110 cycles/minute), left thoracotomy was performed to expose the heart. A site of the left coronary artery at a distance of 2 to 3 mm from the origin of the left coronary artery was ligated with 7-0 proline suture. Two weeks after the coronary artery ligation, an ADRCs cell cluster was placed on tip-curved forceps, and slid to and set on the infarct site of the left ventricular anterior wall. For a sham group, stabilized fibrin not containing ADRCs was transplanted in the same process.

(6) Animal Experiment Protocol

Two weeks after the coronary artery ligation, rats were divided into 5 groups, and then treated as follows. Specifically, prepared were: a group in which an ADRCs cell cluster was transplanted to the left ventricular anterior wall (an A group; n=26); a group in which an ADRCs cell cluster containing pioglitazone (PGZ, 50 mM) was transplanted (an AP group; n=26); a sham group in which no cell cluster transplantation was conducted (an S group; n=26); and a group with direct intramyocardial transplantation (an im group; n=6) and a group with intracoronary transplantation (an is group; n=6) of ADRCs to peri-infarct regions of the left ventricular anterior walls. Then, histological evaluation and molecular evaluation were conducted on days 12 and 56 after the surgery. In addition, the cardiac function was evaluated by echocardiography every week after the surgery.

(7) Echocardiographic Examination

After a sedation state was obtained by inhalation anesthesia of isoflurane, short axis views of the left ventricle at the papillary muscle level were obtained using a echocardiographic system equipped with a 14 MHz transducer. The left ventricular end-diastolic diameter (LVEDd) and end-systolic diameter (LVESd) were measured. The measurements were repeated three times or more, and the average values were obtained. The left ventricular ejection fraction (EF %) was calculated from the following equations.

Left ventricular ejection fraction(EF)={(LVEDV−LVESV)/LVEDV}×100=(SV/LVEDV)×100

Left ventricular end-diastolic volume(LVEDV)={7.0/(2.4+LVEDd)}×LVEDd$^3$

Left ventricular end-systolic volume(LVESV)={7.0/(2.4+LVEDs)}×LVEDs$^3$ (8) Histological Evaluation On days 14 and 56 after the surgery, a sedation state was obtained by inhalation deep anesthesia of isoflurane, and thereafter the heart continuously beating was removed. Each tissue section was prepared by slicing the left ventricle in the short axis direction, compound-embedding the slice, and freezing the slice in liquid nitrogen. Hematoxylin-eosin staining, Picro-Sirius red staining, Masson trichrome staining, Oil Red O staining, adiponectin immunostaining, SMA immunostaining, and von Willebrand factor immunostaining were performed. The fibrosis rate was determined by analysis of a Picro-Sirius red stained image. For the living cell size at the peri-infarct border site, the cell short diameter in one field of view (at a magnification of 400) of a hematoxylin-eosin stained image was measured and the average value of 10 fields of view per sample was calculated. In addition, the number of capillaries per field of view (at a magnification of 400) of a von Willebrand factor immunostained image was measured, and the average value of 5 fields per sample was calculated.

(9) Molecular Biological Study

On days 14 and 56 after the transplantation, the removed cardiac sample was divided into an infarct part (scar), a border part between the infarct and normal parts (border), and a non-infarct part (remote), and mRNA extraction in each of the parts was carried out. Then, cDNA was synthesized from mRNA by reverse transcription reaction. The transcription level of each of vascular endothelial cell growth factor (VEGF), adiponectin (APN), adiponectin receptor-1 (Adipo-R1), adiponectin receptor-2 (Adipo-R2), T-cadherin (CDH-13), and tumor necrosis factor (TNF-α) was quantified by the quantitative PCR method, and was divided by the transcription level of glyceraldehyde-3-phosphate dehydrogenase (GAPDH), which is an endogenous control. Then, a ratio of the obtained value to the normal value of each sample was expressed.

(10) Statistical Analysis

Data was expressed as the average value±standard error. Comparison between groups was conducted by t test, and a P value less than 0.05 was considered to indicate a significant difference. For survival rate analysis, the survival rate was calculated by the Kaplan-Meier method, and a significant difference for each experimental group was determined by a log rank test.

[Results]

Figure 1B:
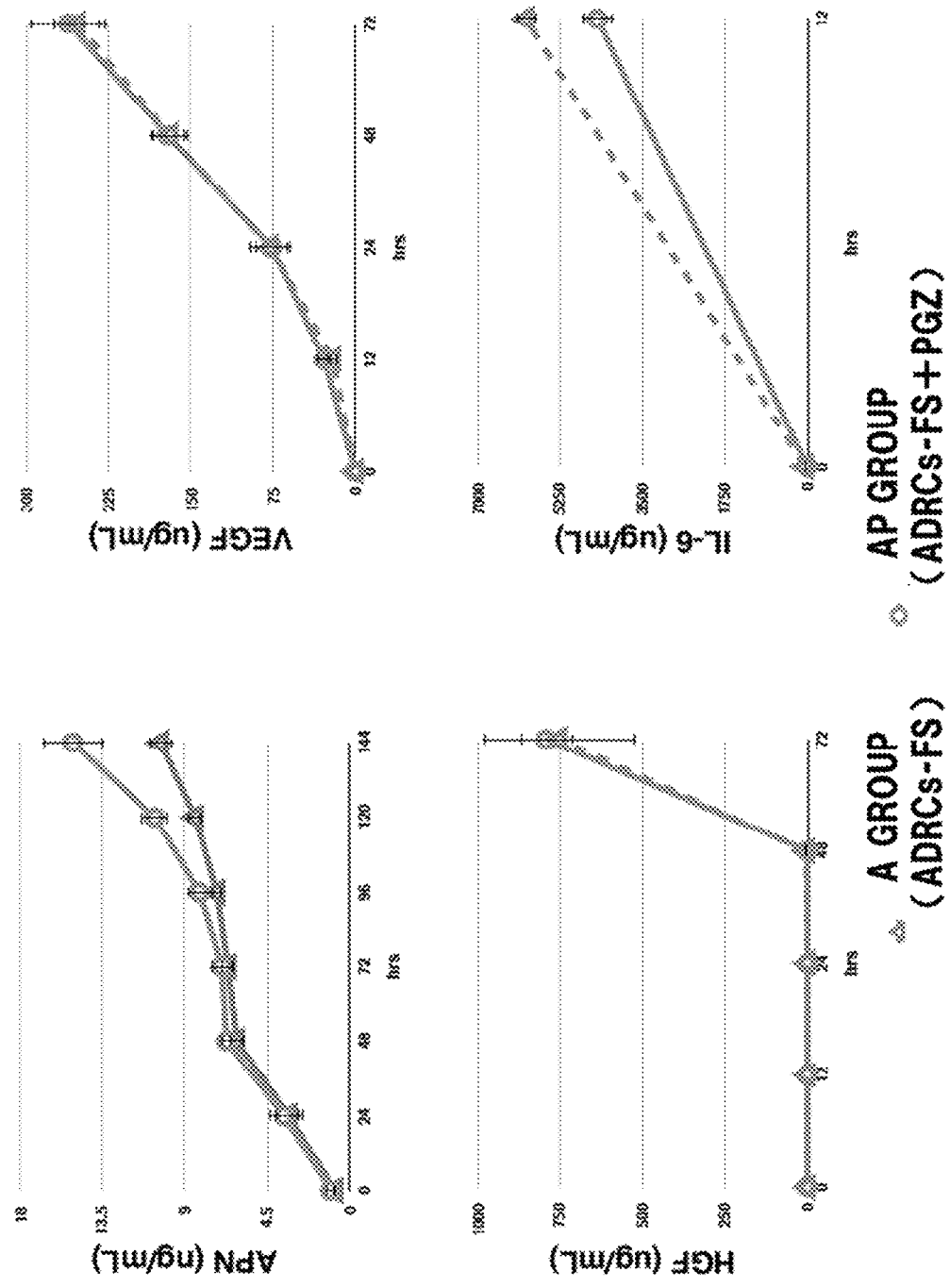

(1) ADRCs Cell Cluster's Abilities to Secrete Cytokines and Differentiate into Adipocytes ADRCs cell clusters (FIG. 1A) and pioglitazone (PGZ)-containing ADRCs cell clusters were prepared and cultured for 144 hours in a humid environment at 37° C. in a 5% carbon dioxide atmosphere, and then their cytokine secretion abilities were examined. The amounts of adiponectin (APN), VEGF, HGF, and IL-6 secreted from the ADRCs cell clusters and the PGZ-containing cell clusters increased over time in the culture media. The adiponectin concentrations after culture for 144 hours in particular were $21.7\pm0.9$ $ng/5\times10^6$ cells/day and $51\pm3.9$ $ng/5\times10^6$ cells/day, respectively, and the culture medium of the PGZ-containing ADRCs cell cluster has a significantly higher concentration than that of the cell cluster containing only ADRCs (FIG. 1B).

Figure 1C:
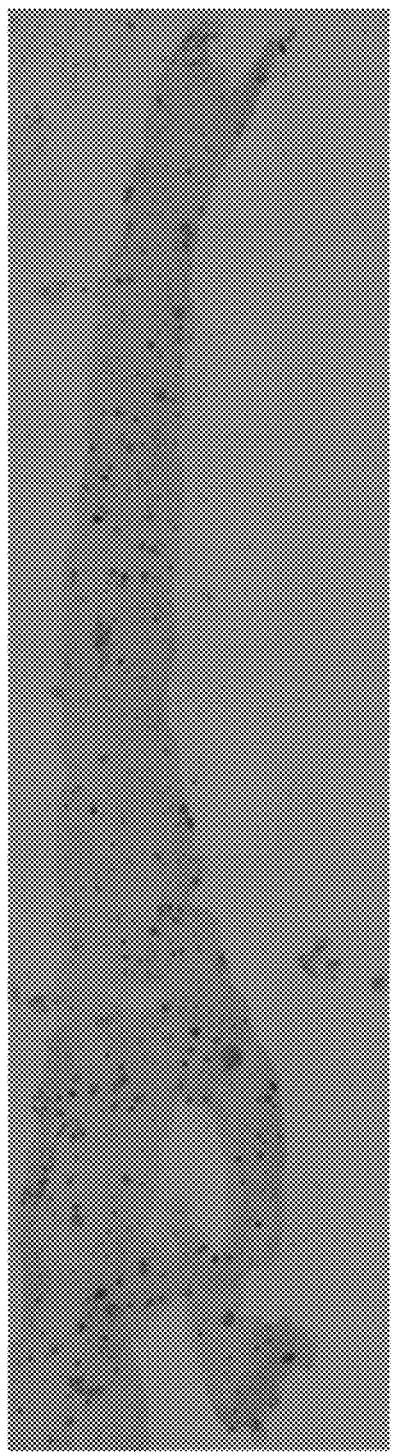

Also, the ADRCs cell cluster was treated with 10 to 15% autoserum or fetal bovine serum (FBS), 0.5 to 2.0 μM insulin, 0.1 to 1.0 μM dexamethasone, and 0.2 to 2 mM isobutyl-methylxanthine, and thereby were induced to differentiate into adipocytes. As a result, adipocytes positive for Oil Red O appeared 7 days after the induction of differentiation (FIG. 1C). The number of cells constituting one cell cluster was in the order of $5\times10^6$ and the cell cluster contained Oil Red O positive cells with a thickness of about 1000 μm. Thus, it was found that the cell cluster maintained the differentiation ability.

(2) Engraftment of ADRCs Cell Cluster on Myocardial Surface

Figure 2A:
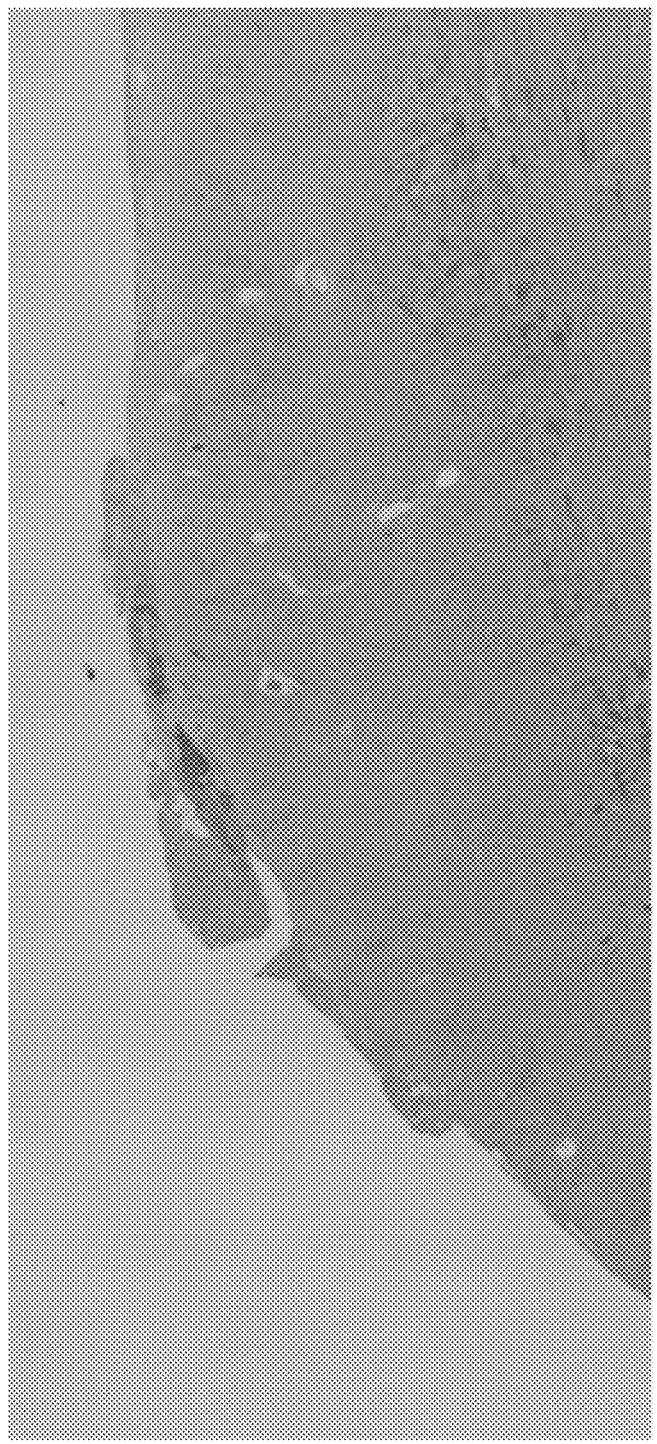
FIG. 2A is a photomicrograph (in vivo evaluation) of a cardiac tissue of a myocardial infarction model rat taken on day 5 after transplantation of an ADRCs cell cluster into the rat.
Figure 2B:
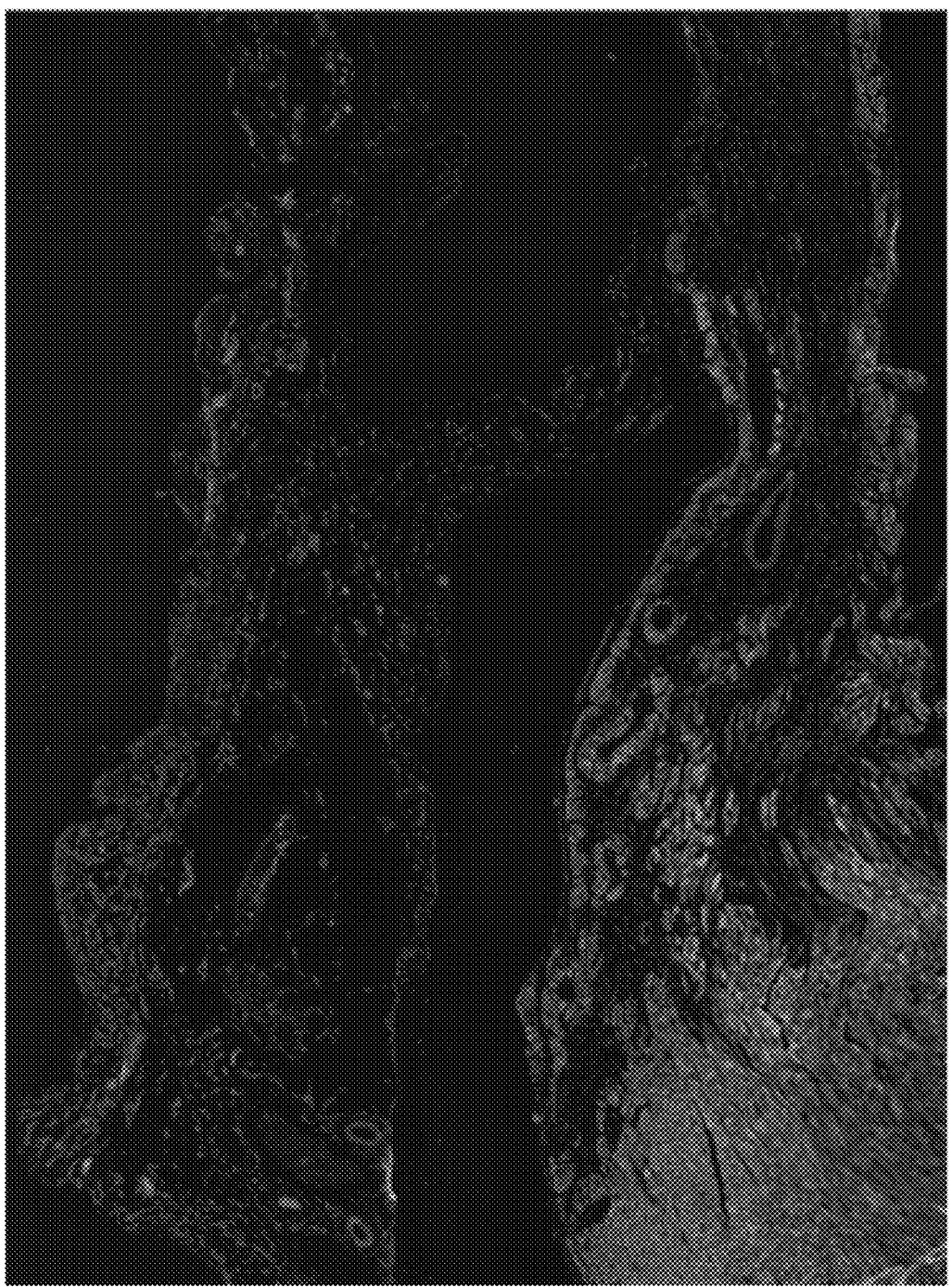
FIG. 2B is a photomicrograph (in vivo evaluation) demonstrating the expression of neovascularization on the epicardial side and between the cell cluster and the area of myocardial infarction.

In order to examine the engraftment of an ADRCs cell cluster on the cardiomyocyte, the cell clusters were transplanted to the cardiomyocyte of rats promptly after the preparation. As a result, the cell cluster after several days to one week adhered to the cardiac surface (FIG. 2A). Since the cell cluster was observed communicating with the cardiomyocyte via capillary vessels (FIG. 2B), it was confirmed that the transplanted cell cluster was successfully engrafted on the cardiomyocyte.

(3) Influence of Transplantation of ADRCs Cell Cluster on Cardiac Function

FIGS. 3A-3D demonstrate evaluation results of the cardiac function on day 28 after the ADRCs cell cluster transplantation on chronic myocardial infarction model rats. Here, the left ventricular ejection fraction (EF), left ventricular end-systolic diameter (LVESd), left ventricular end-diastolic diameter (LVEDd), and left-ventricular end-diastolic wall thickness (LVAWD) in heart echocardiographic examinations were used as evaluation indexes of the cardiac function. Two weeks after coronary artery ligation, model rats were divided into 5 groups and tested after the following treatments. Specifically, tested were the group in which an ADRCs cell cluster was transplanted to the left ventricular anterior wall (the A group); the group in which an ADRCs cell cluster containing pioglitazone (PGZ, 50 mM) was transplanted to the left ventricular anterior wall (the AP group); the sham group in which no cell cluster transplantation was conducted (the S group); and the group with direct intramyocardial transplantation (the im group) and the group with left ventricular intracoronary transplantation (the is group) of ADRCs to the peri-infarct regions of the left ventricular anterior walls.

Figure 3B:
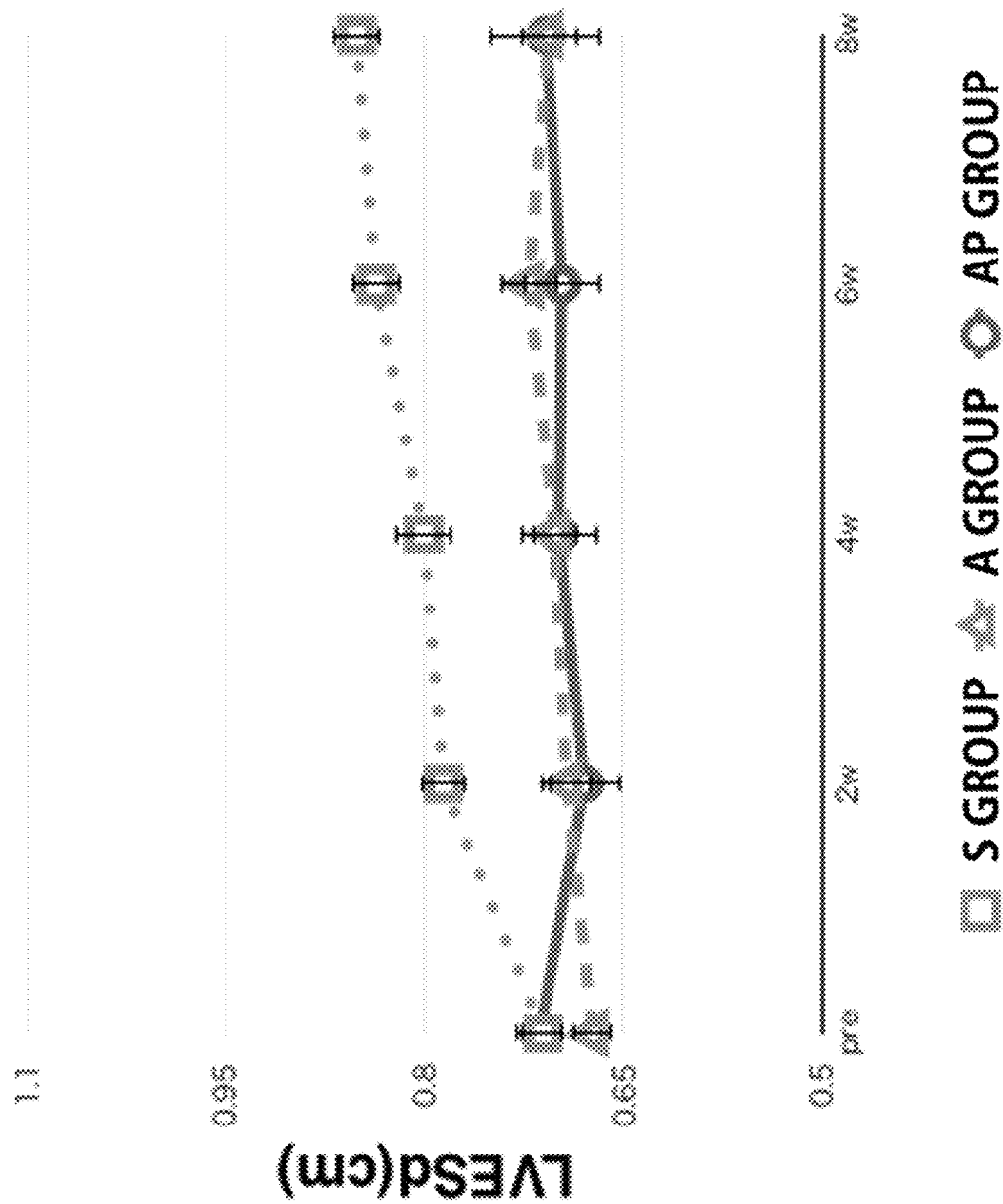
Figure 3D:
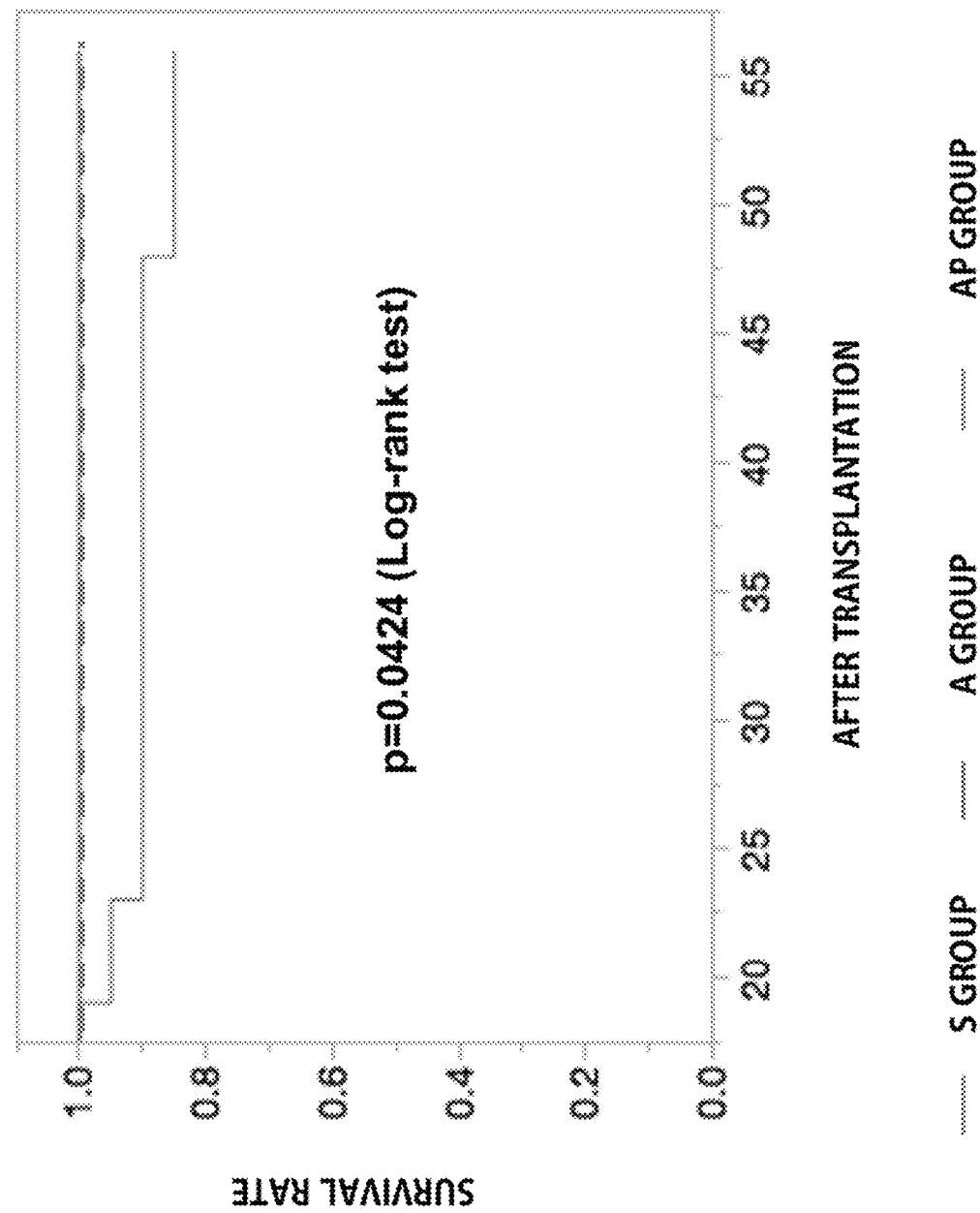

From the echocardiographic examinations of the hearts, the A group and the AP group had significantly larger EF values than the S group, and were found to have an improvement of left ventricular contractility. Furthermore, at week 8 after the transplantation, the AP group demonstrated greater improvement in EF than the A group (FIG. 3A). Meanwhile, as compared with the S group, the A group and the AP group had the LVEDd values with no significant difference (FIG. 3C), and had small LVESd values (FIG. 3B). Therefore, the A group and the AP group were observed having an improvement of left ventricular contractility by the transplantation. In addition, the survival rates of the groups were evaluated. As a result, the survival rates of the A group and the AP group were significantly higher (p=0.0424) than that of the S group (FIG. 3D). From the above results, transplantation of ADRCs cell clusters was found to have an excellent therapeutic effect on myocardial infarction.

Figure 4B:
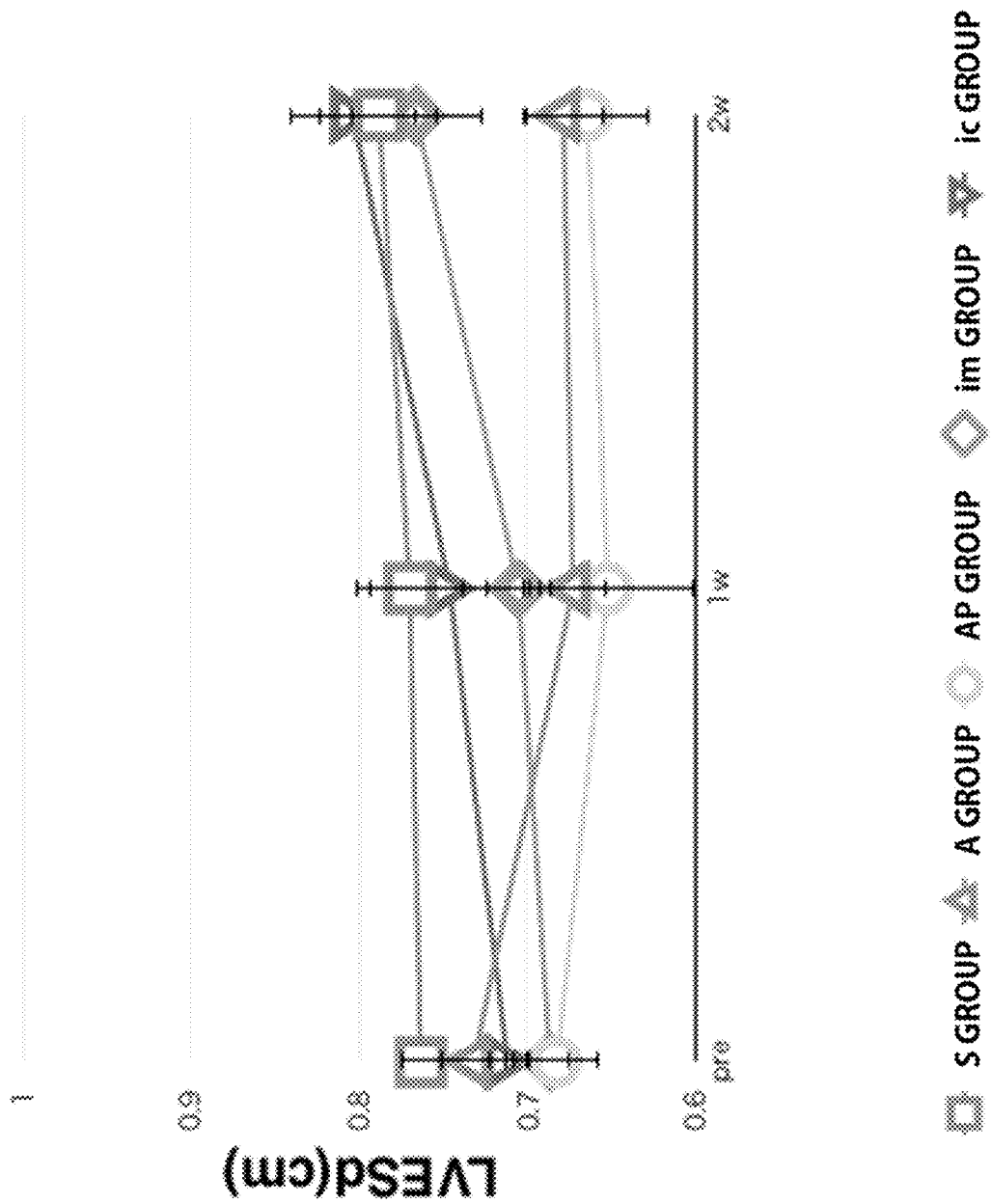
Figure 4C:
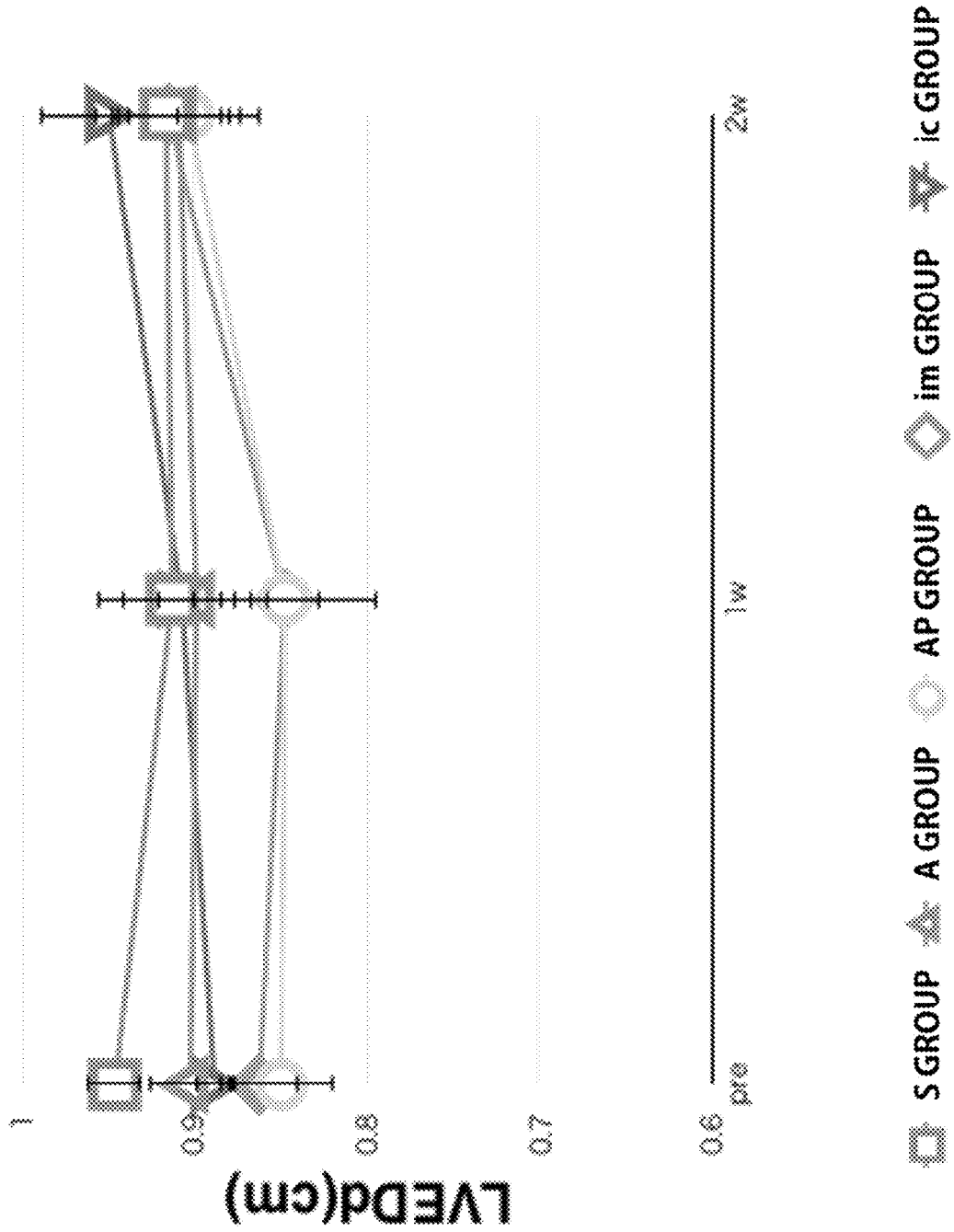

Furthermore, as a result of comparative tests with the administration methods different from the transplantation of a ADRCs cell cluster, that is, with the group with direct intramyocardial transplantation (the im group) and the group with left ventricular intracoronary transplantation (the ic group) of ADRCs to the peri-infarct regions of the left ventricular anterior walls, the A and AP groups had the EF values significantly larger than those of the S, im, and ic groups (FIG. 4A), had the LVESd values smaller than those of the S, im, and ic groups (FIG. 4B), and had no significant difference in LVEDd (FIG. 4C). The results described above demonstrate that the transplantation of an ADRCs cell cluster has a superior therapeutic effect in the treatment of myocardial infarction to that of the method of directly injecting ADRCs into the cardiomyocyte or the coronary artery.

(4) Influence on Myocardial Tissue by Transplantation of ADRCs Cell Cluster

Figure 5B:
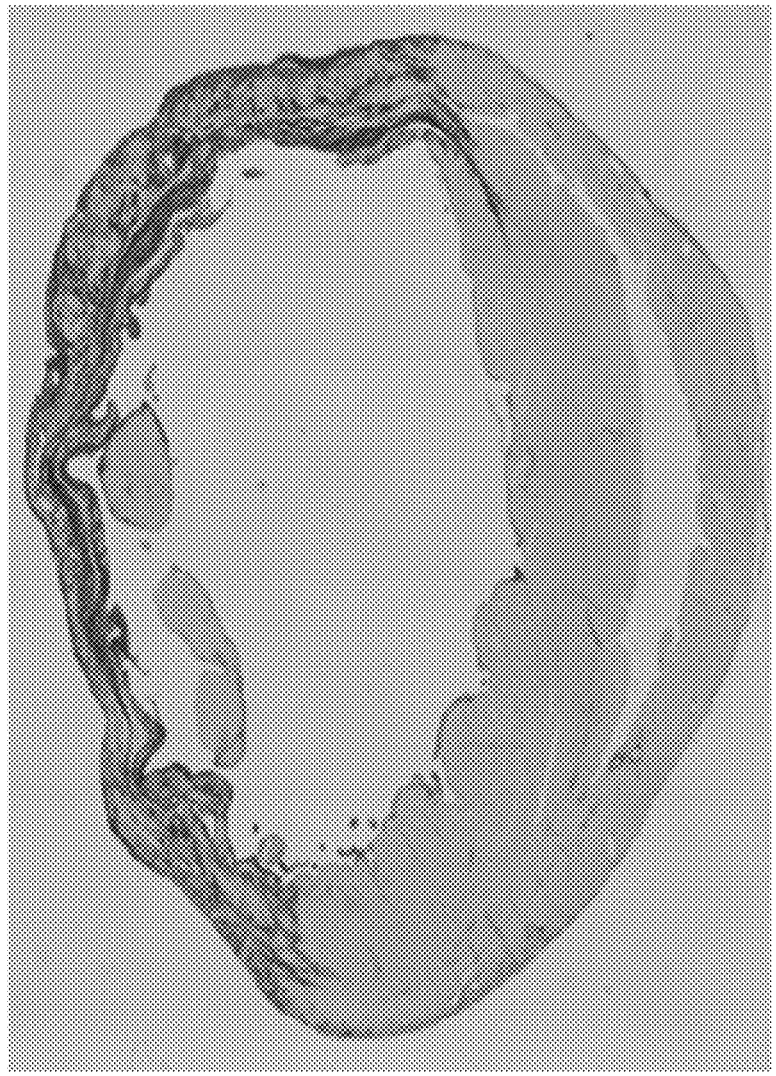
Figure 5C:
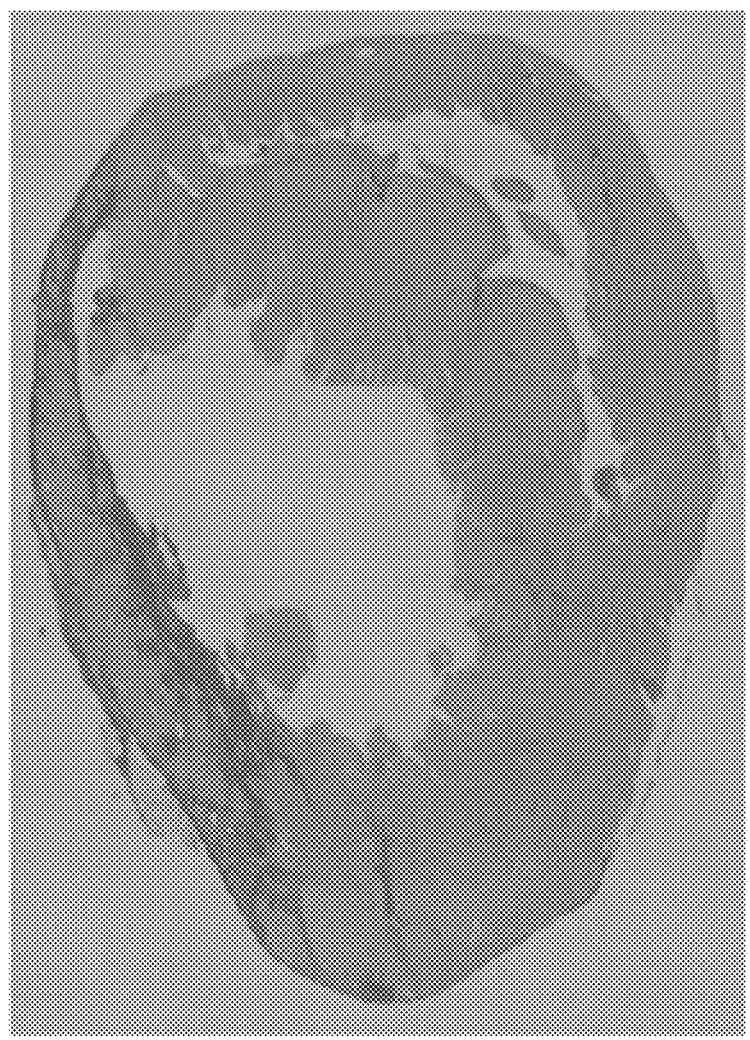
Figure 5E:
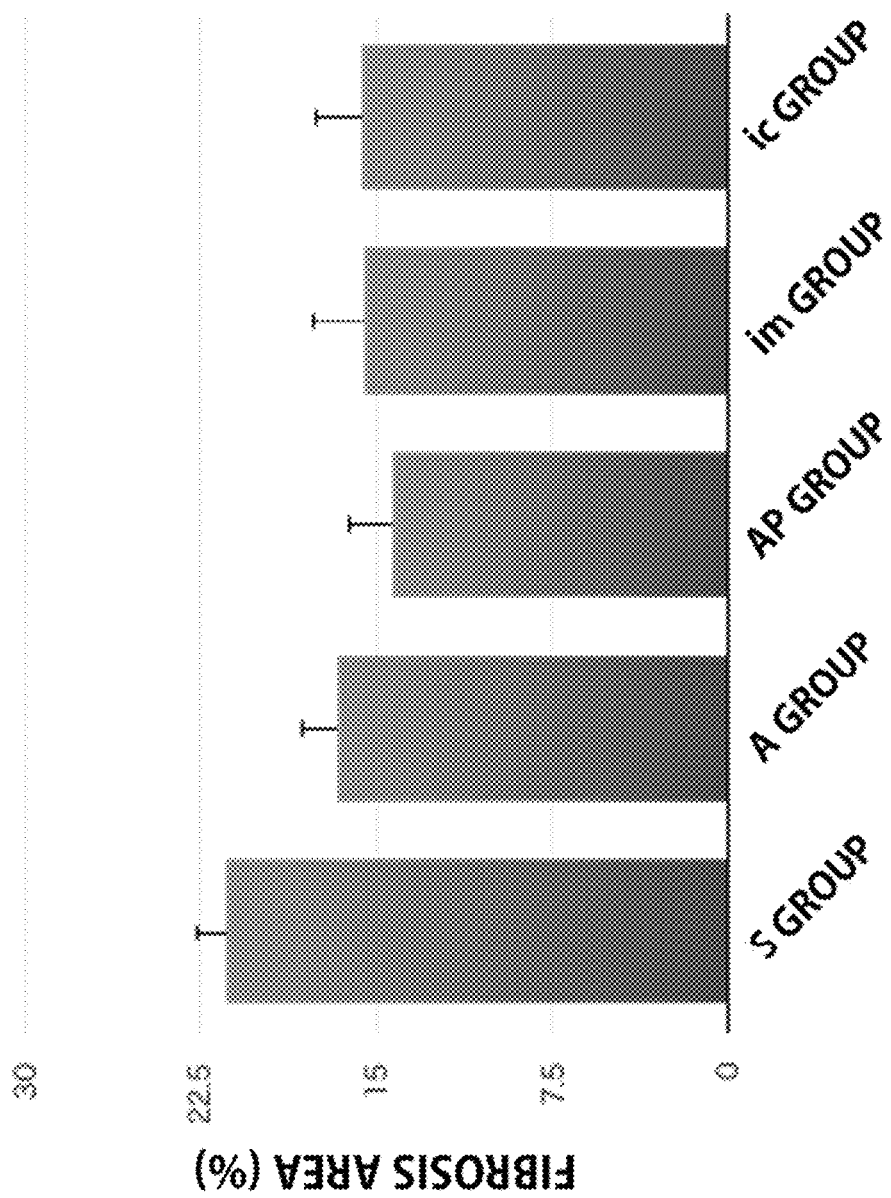
Figure 5F:
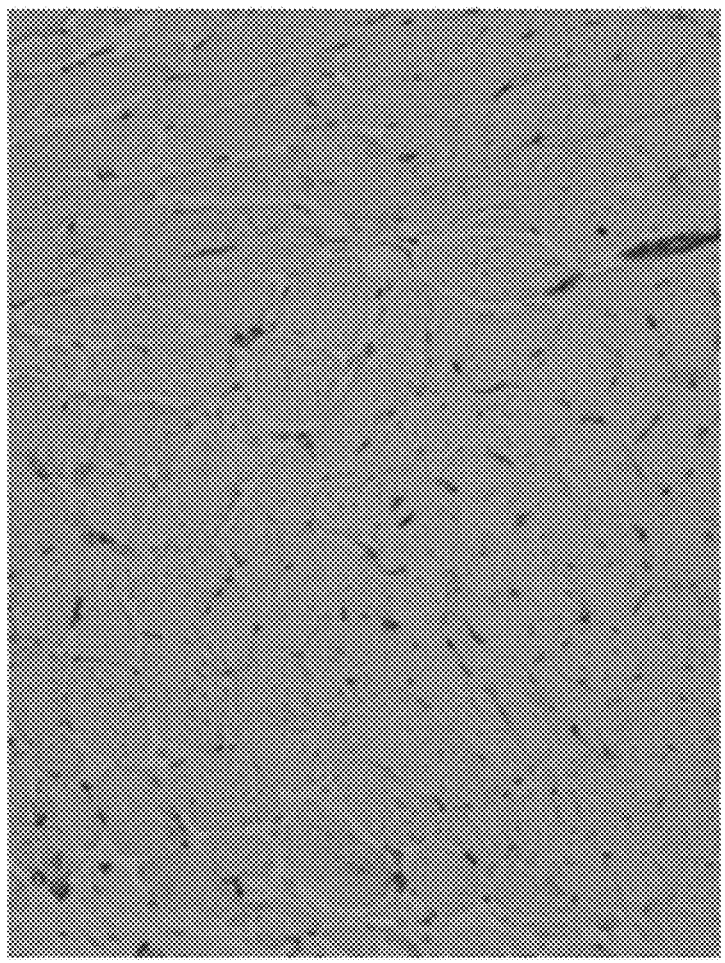
Figure 5G:
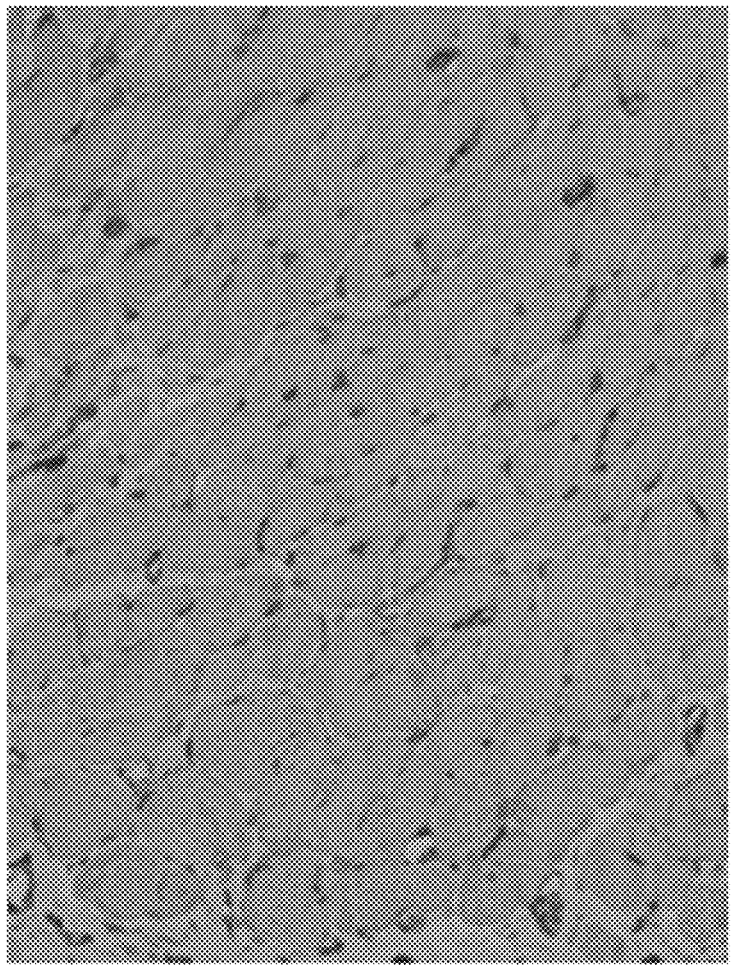
Figure 5H:
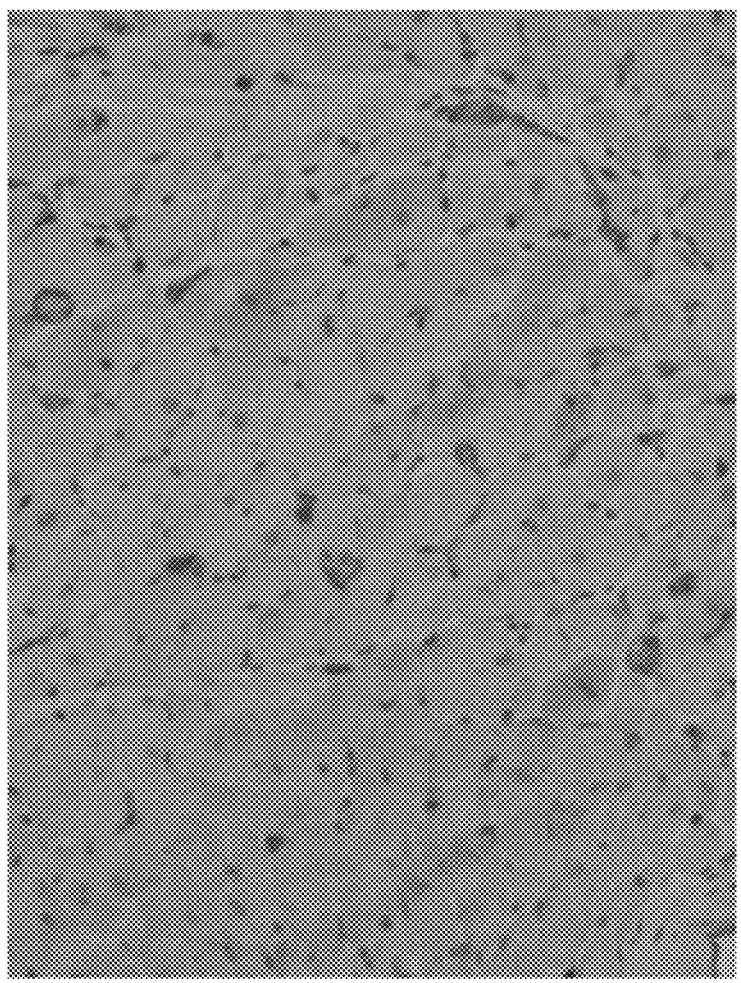
Figure 5I:
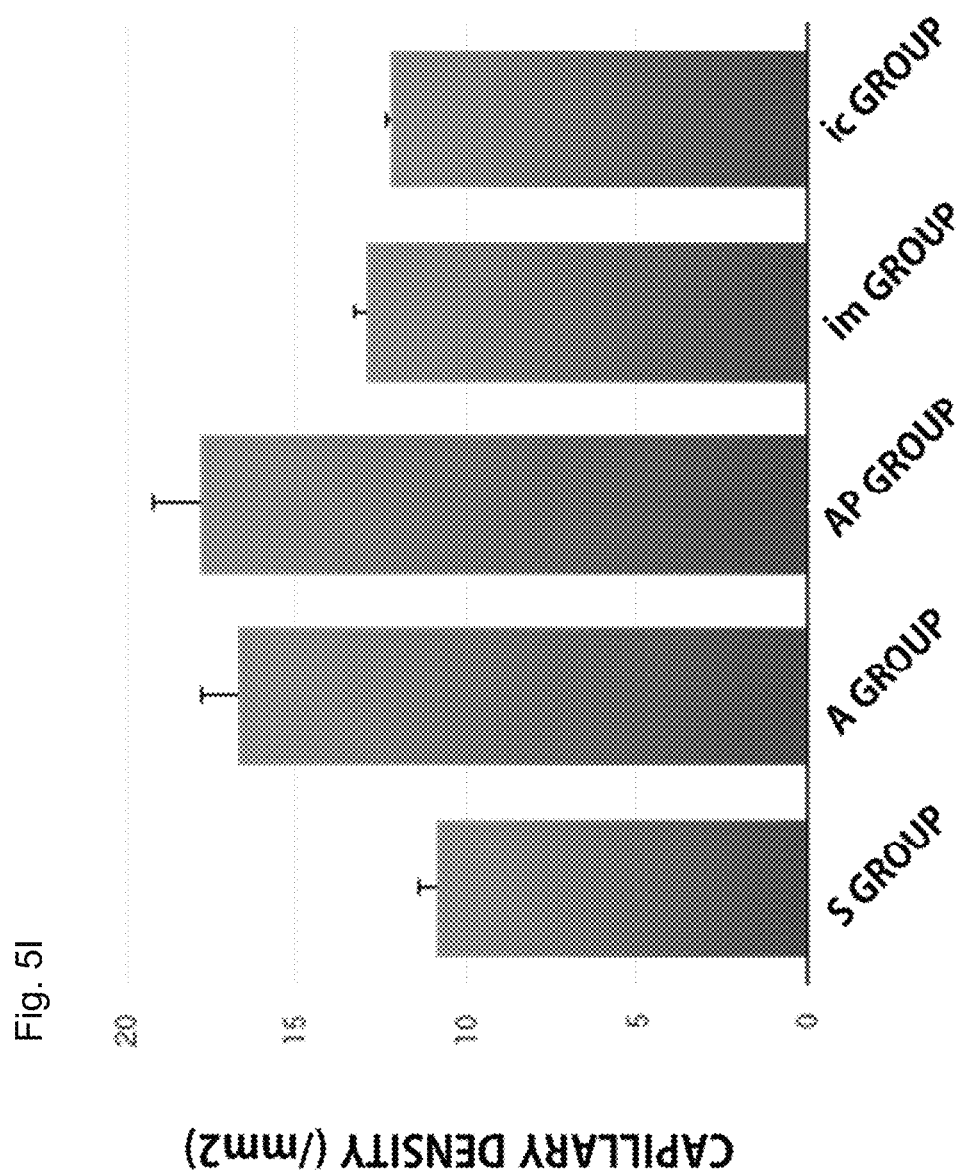

Histological analysis was performed on days 14 and 56 after the ADRCs cell cluster transplantation to the myocardial infarction model rats. The untreated S group demonstrated strong thinning of the left ventricular anterior wall (FIG. 5A), whereas the A group (FIG. 5B) and the AP group (FIG. 5 C) were found to have the left ventricular anterior walls thicker than those of the S group, the im group, and the ic group, and maintain the left ventricular anterior wall tissue (FIG. 5D). As a result of the quantification of the infarct size, the A group and the AP group tend to be smaller in infarct size than the S group, the im group, and the ic group, although there was no statistically significant difference (FIG. 5E). Furthermore, as a result of the measurement of the capillary density at the peri infarct area, the A group (FIG. 5G) and the AP group (FIG. 5H) demonstrated significantly higher capillary densities than those of the S group (FIG. 5F), the im group, and the ic group (FIG. 5I).

(5) Cardiac Protection Effect by ADRCs Cell Cluster

Figure 6A:
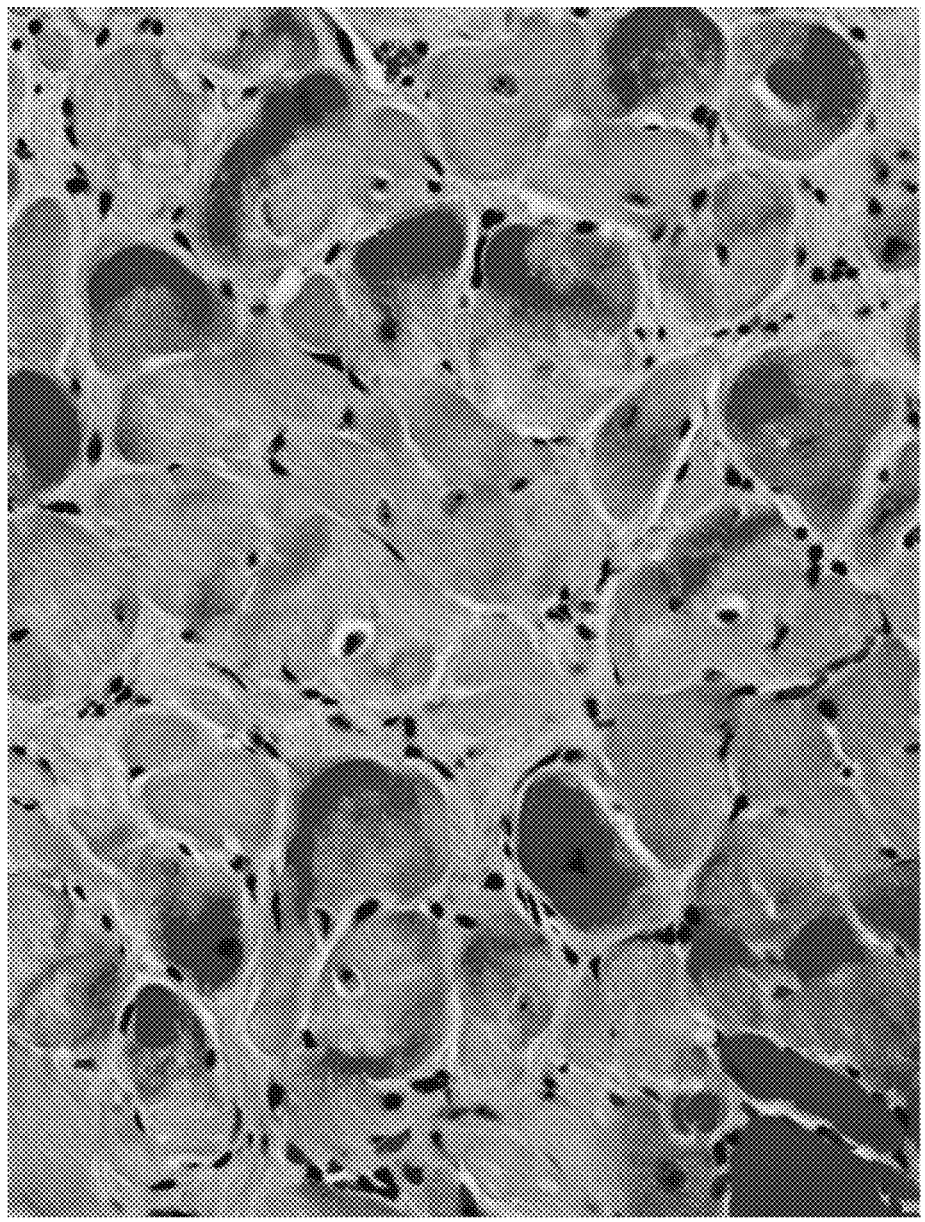
Figure 6B:
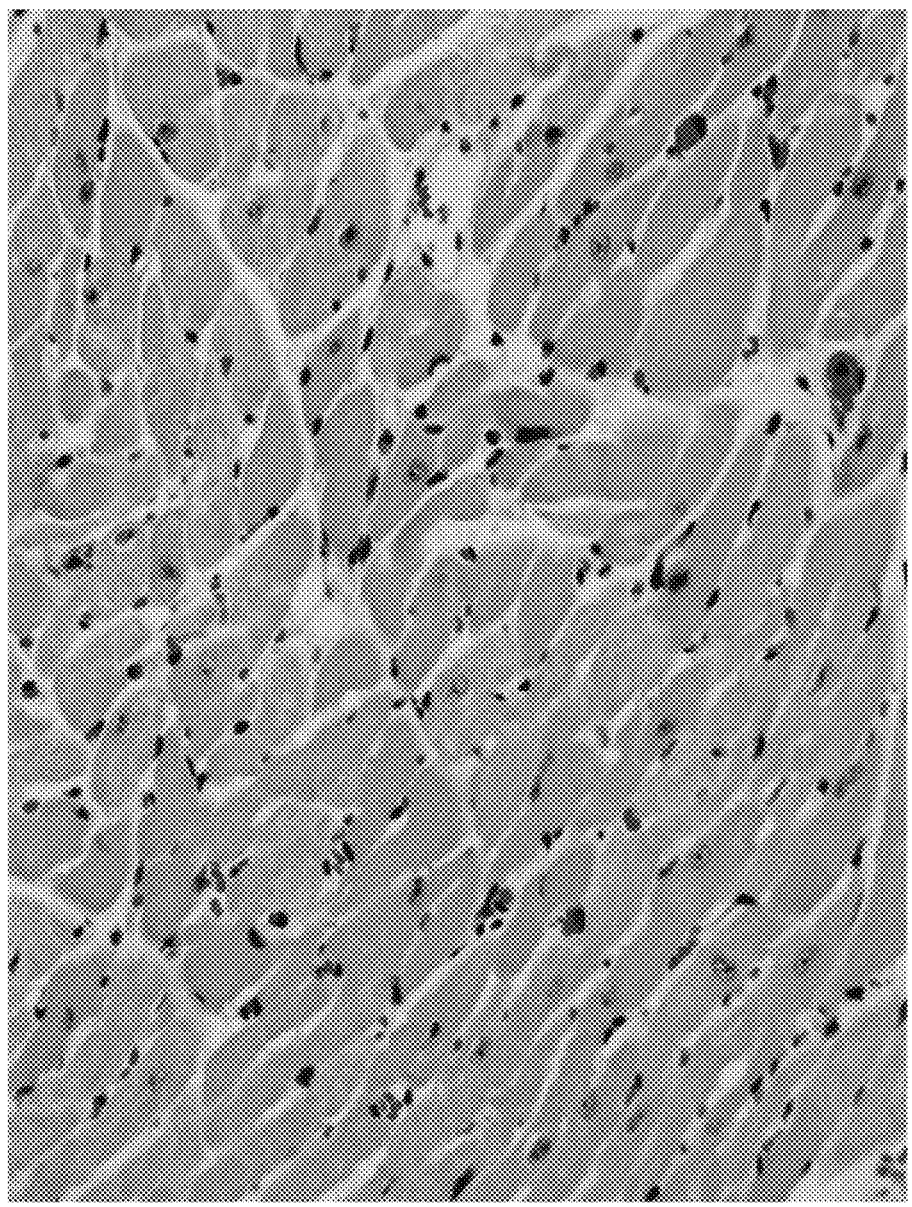
Figure 6D:
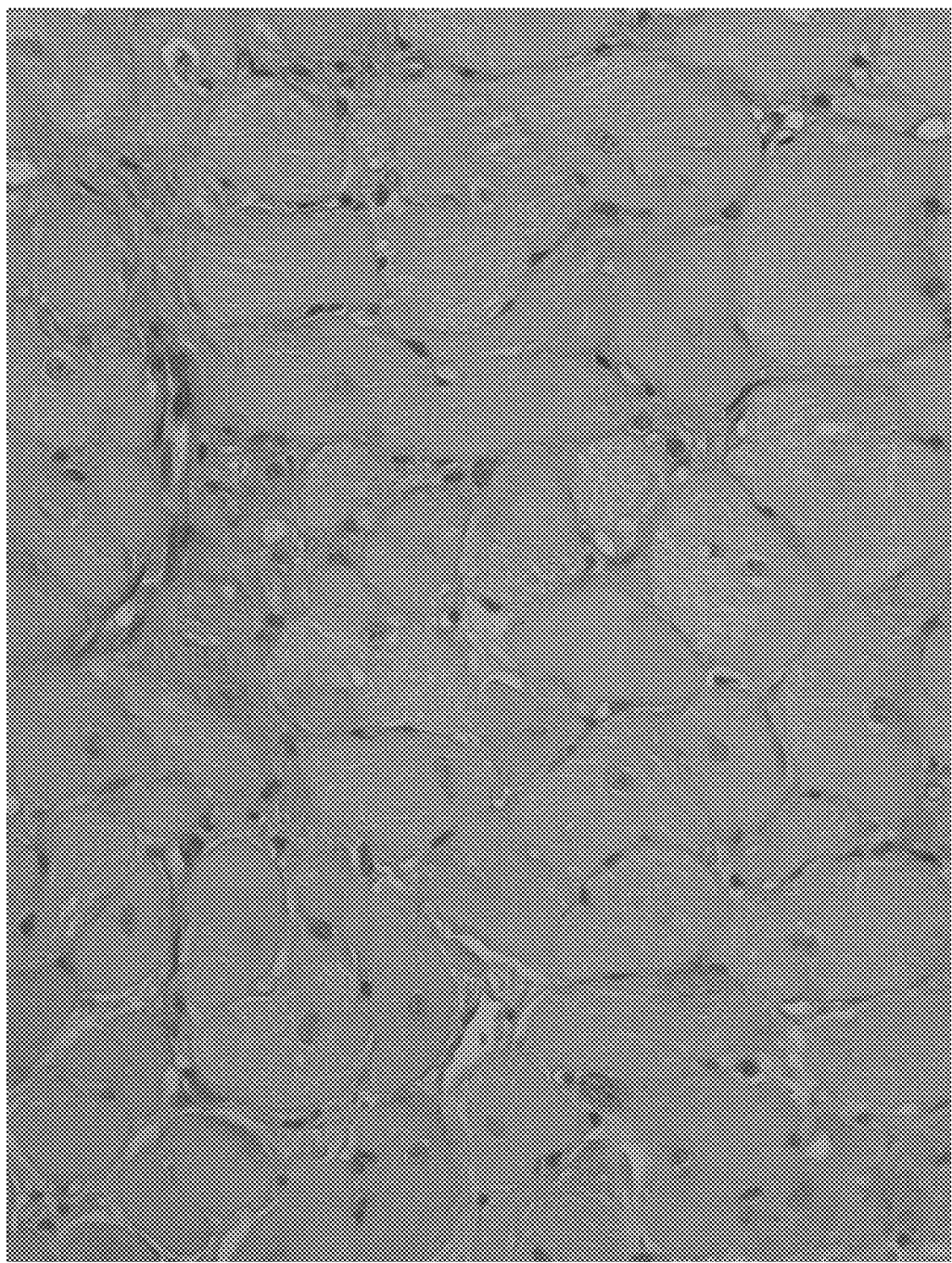
Figure 6E:
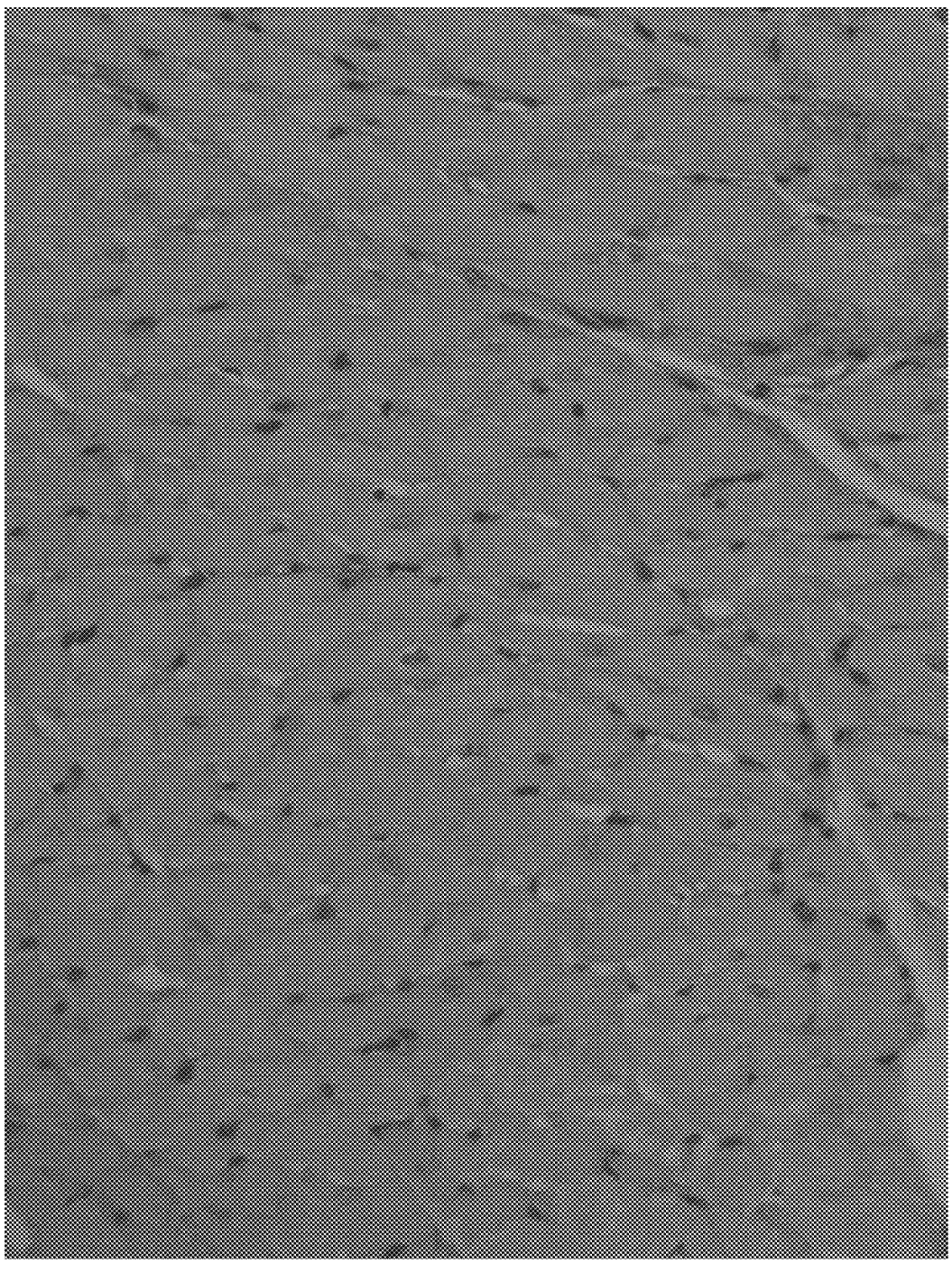
Figure 6F:
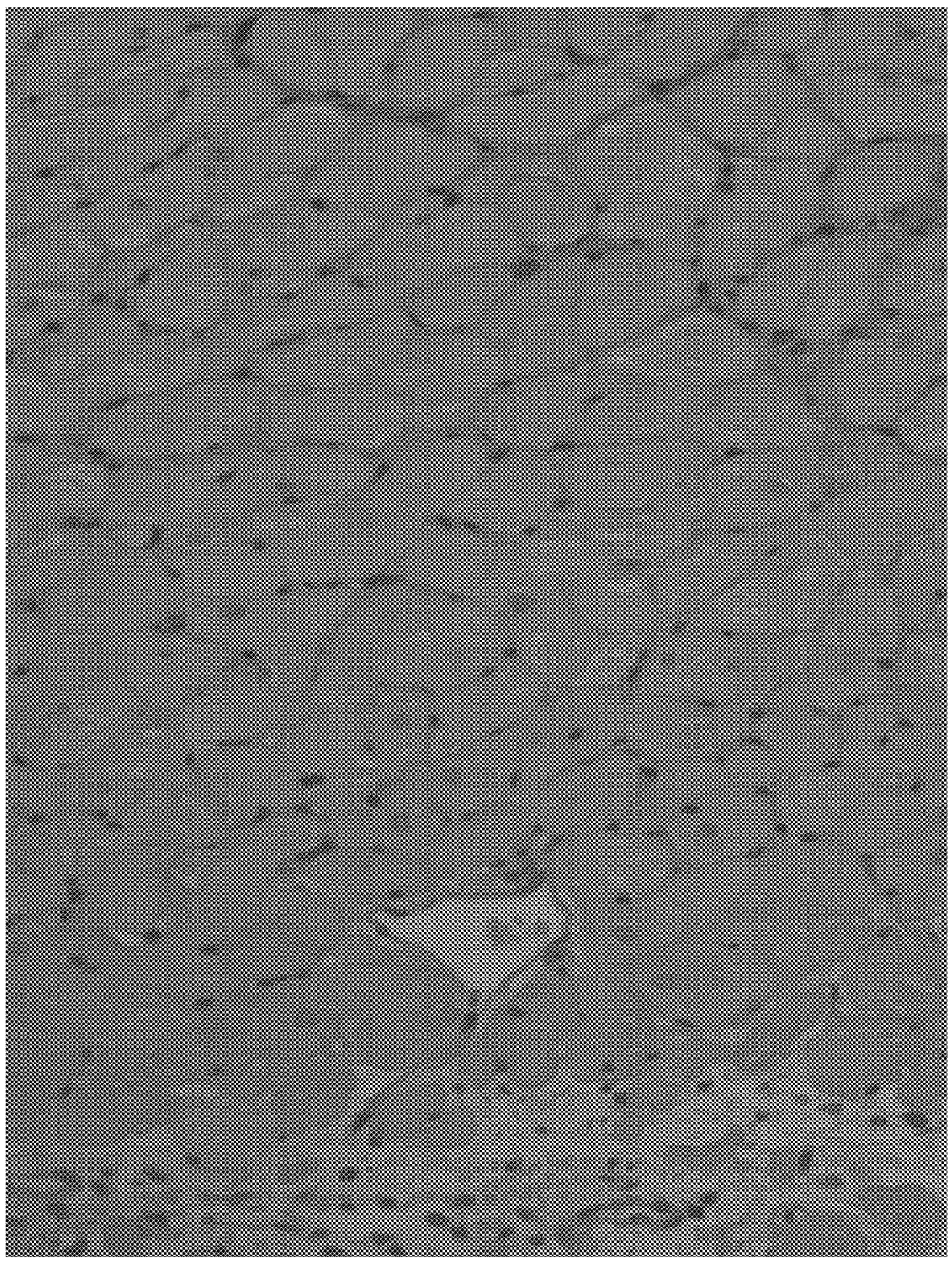
Figure 6G:
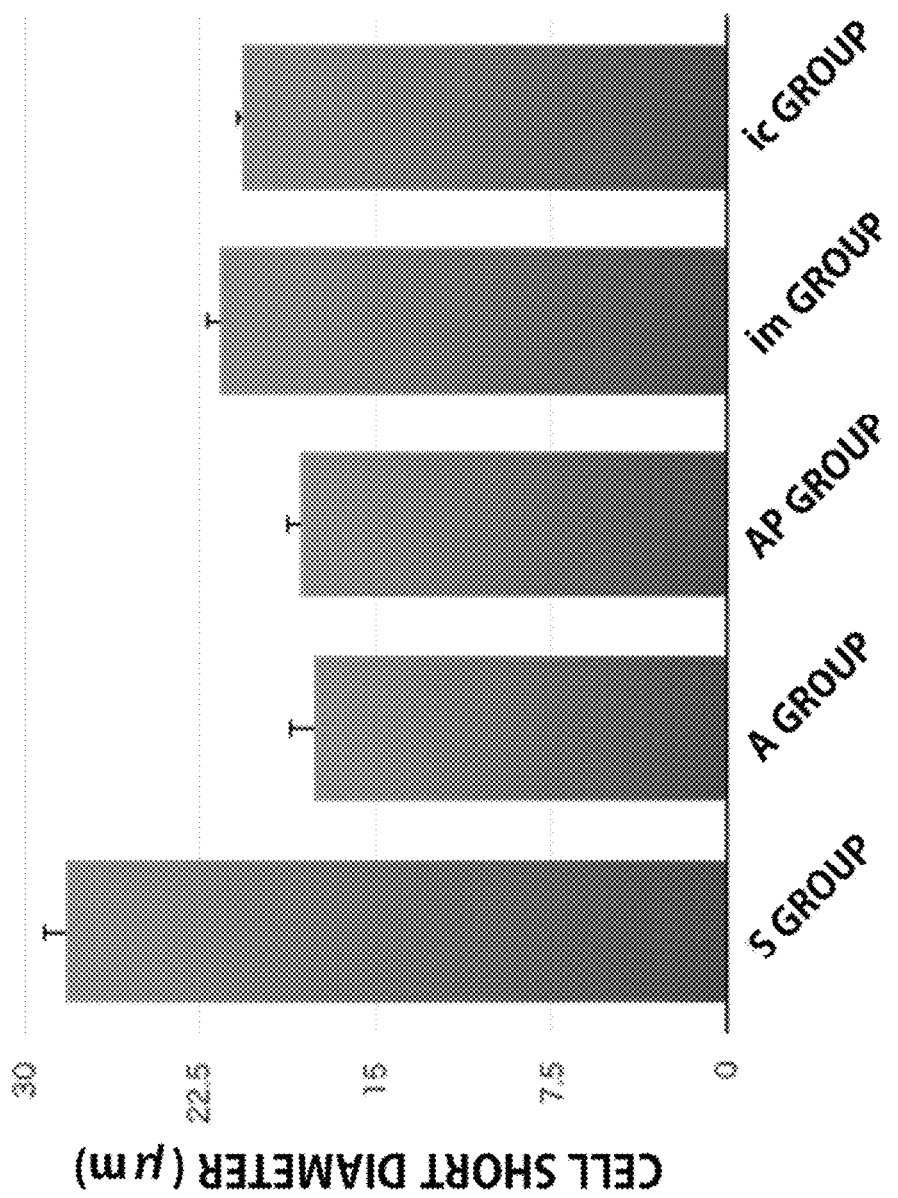

Histological analysis was performed on days 14 and 56 after the ADRCs cell cluster transplantation to the myocardial infarction model rats. A cell diameter at the peri infarct area of each of the groups was detected by hematoxylin-eosin staining (FIGS. 6A to 6 C) and PAS staining (FIGS. 6 D to 6 F), and the cell short diameters in the A group and the AP group had significantly lower values than those of the S group, the im group, and the ic group (FIG. 6G). The above result suggested the possibility that ADRCs cell cluster transplantation may have protective effect such as anti-apoptosis on residual myocardial cells.

(6) Anti-Apoptosis and Anti-Inflammatory Effects by ADRCs Cell Cluster

Figure 7A:
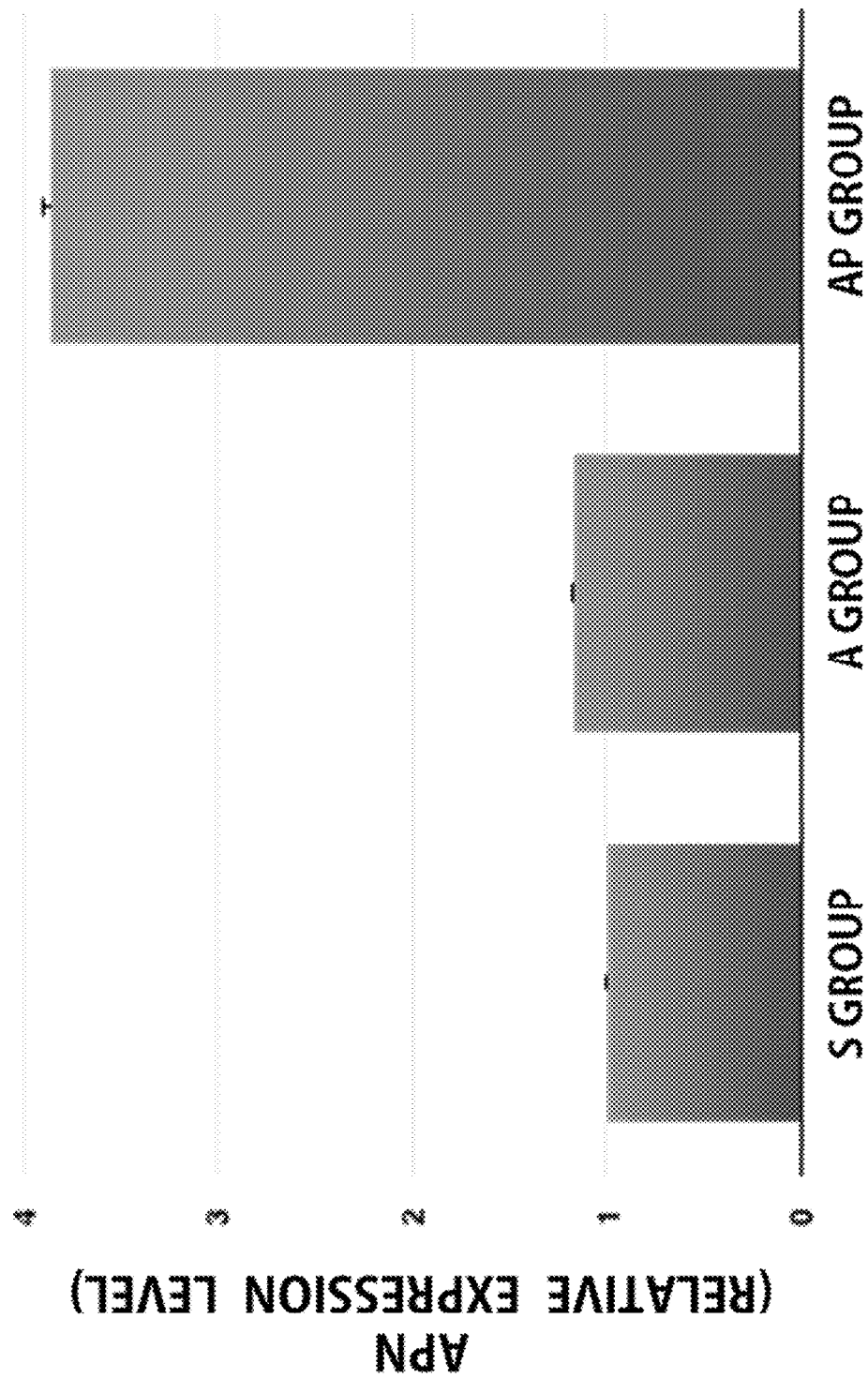
FIGS. 7A-7F include diagrams demonstrating results of examining anti-inflammatory effects by ADRCs cell cluster transplantation.
Figure 7B:
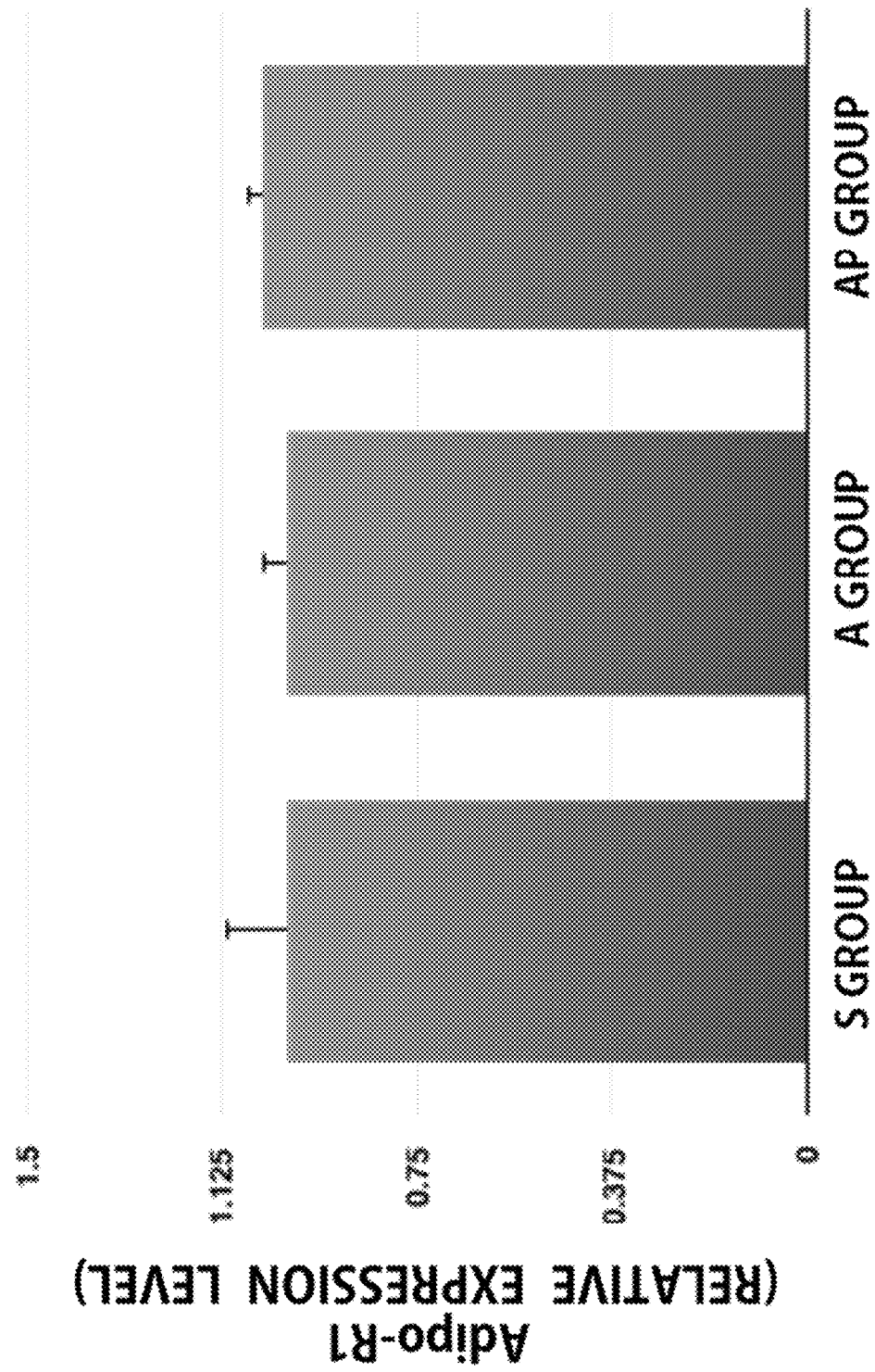
Figure 7C:
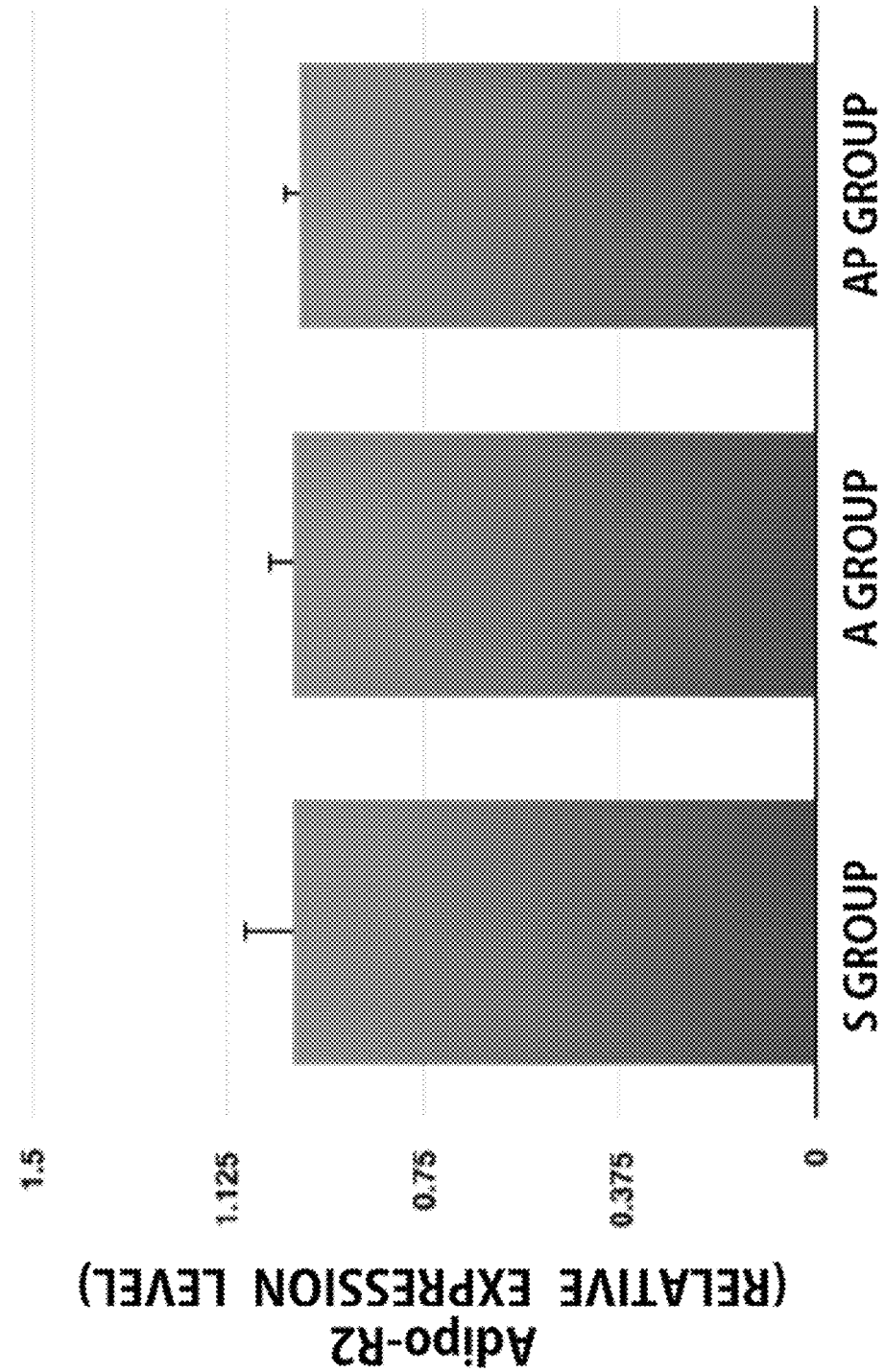
Figure 7D:
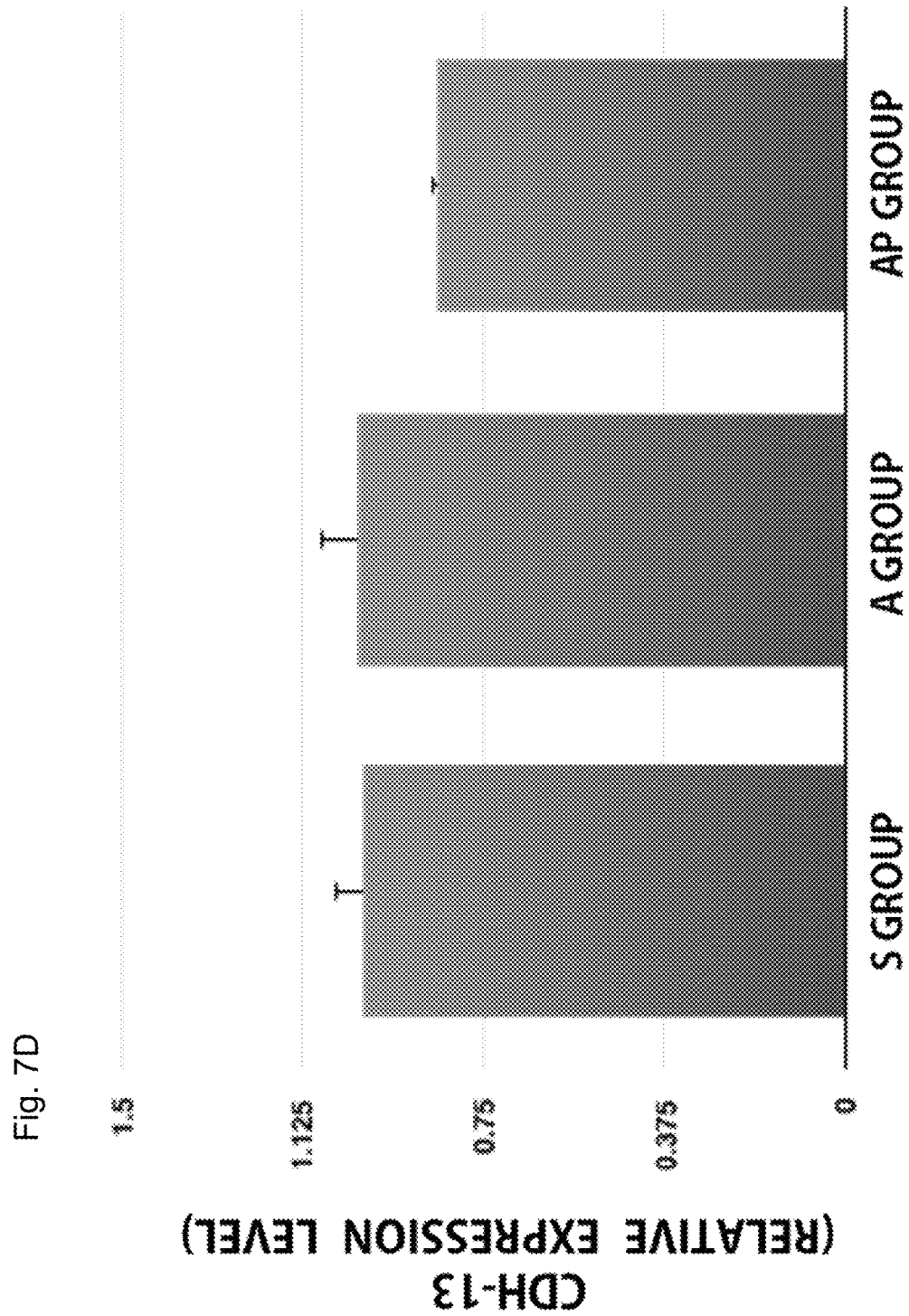
Figure 7E:
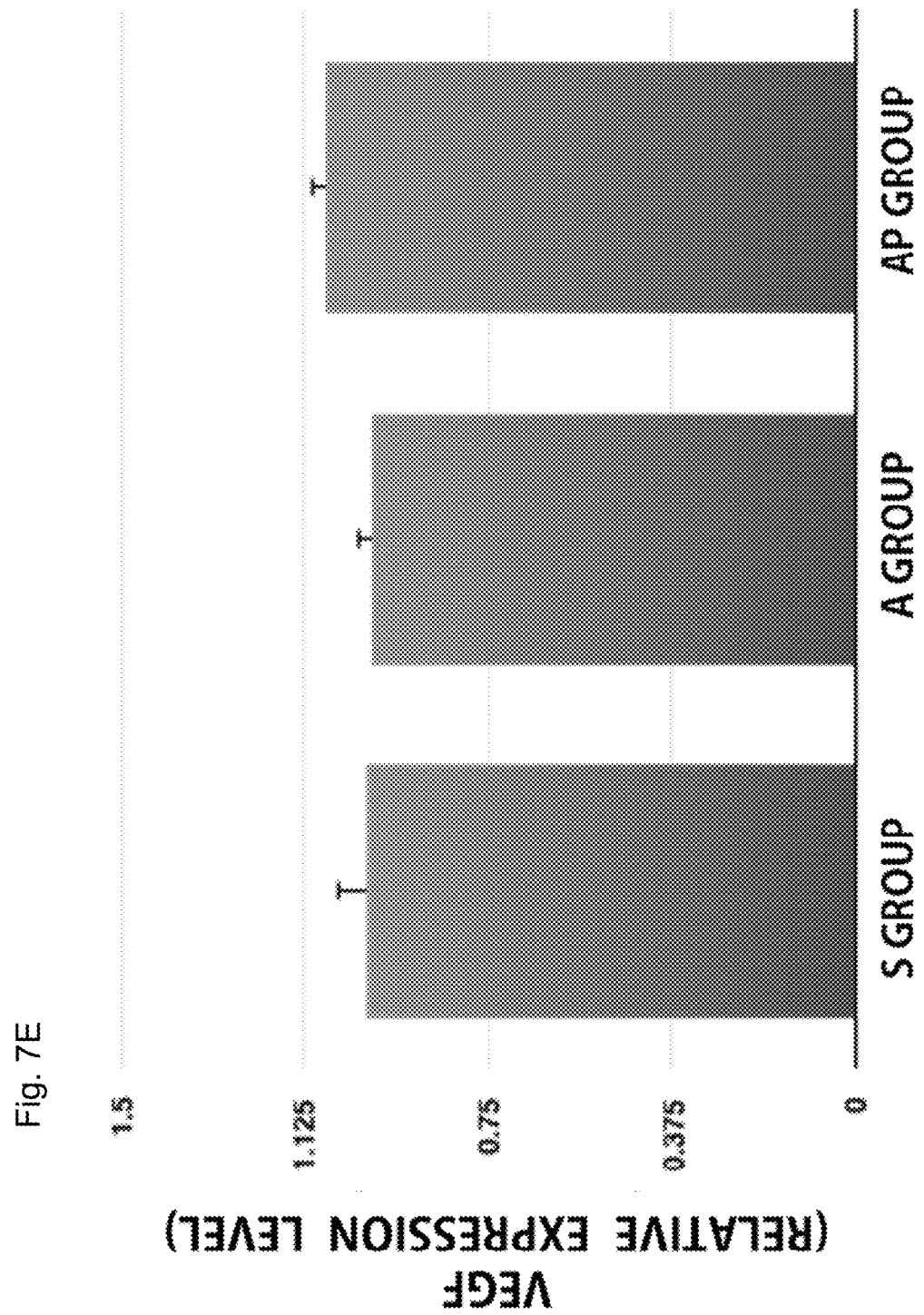
Figure 7F:
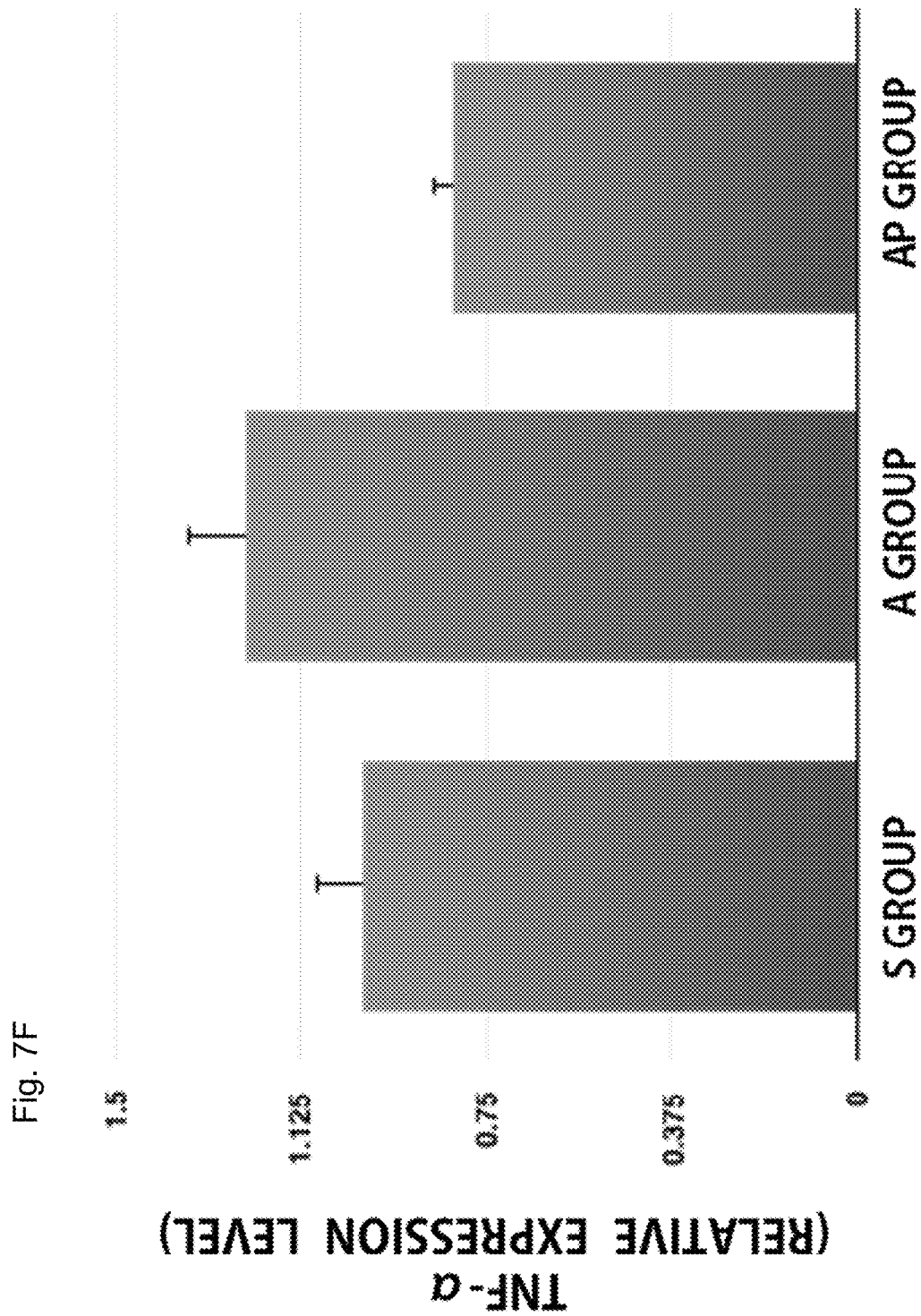

FIGS. 7A-7F show the results of 5 investigations on myocardial protection and anti-inflammatory effects on myocardial tissue on day 56 after the ADRCs cell cluster transplantation. The degrees of transcription of the neovascuralization and myocardial protection cytokines at the peri infarct area of each group were evaluated. As a result, the transcription level of adiponectin (APN) at the periphery of the infarct area was significantly higher in the AP group than in the other groups (FIG. 7A). Also, the group A had a significantly higher APN transcription level than the S group. There was no significant difference in the transcription levels of the other Adipo-R1, Adipo-R2, CDH-13, VEGF, and TNF-α (FIGS. 7B to 7F). The above finding suggested the possibility that the addition of PGZ to the ADRCs cell cluster may further enhance the improvement effect on the cardiac function after myocardial infarction.

Figure 8A:
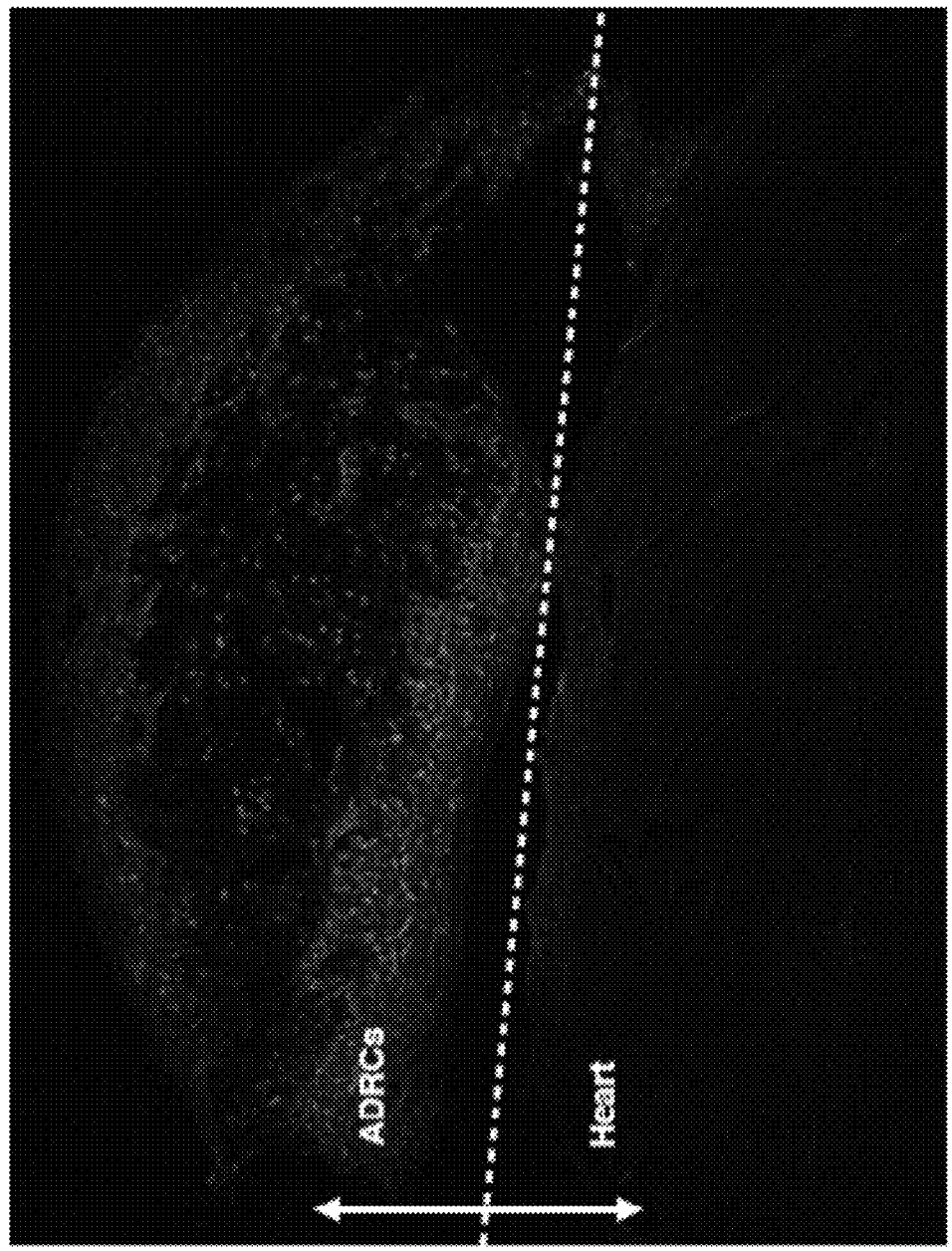
FIGS. 8A-8D include pictures demonstrating an ability to persistently produce adiponectin and successful intramyocardial engraftment of ADRCs.
Figure 8B:
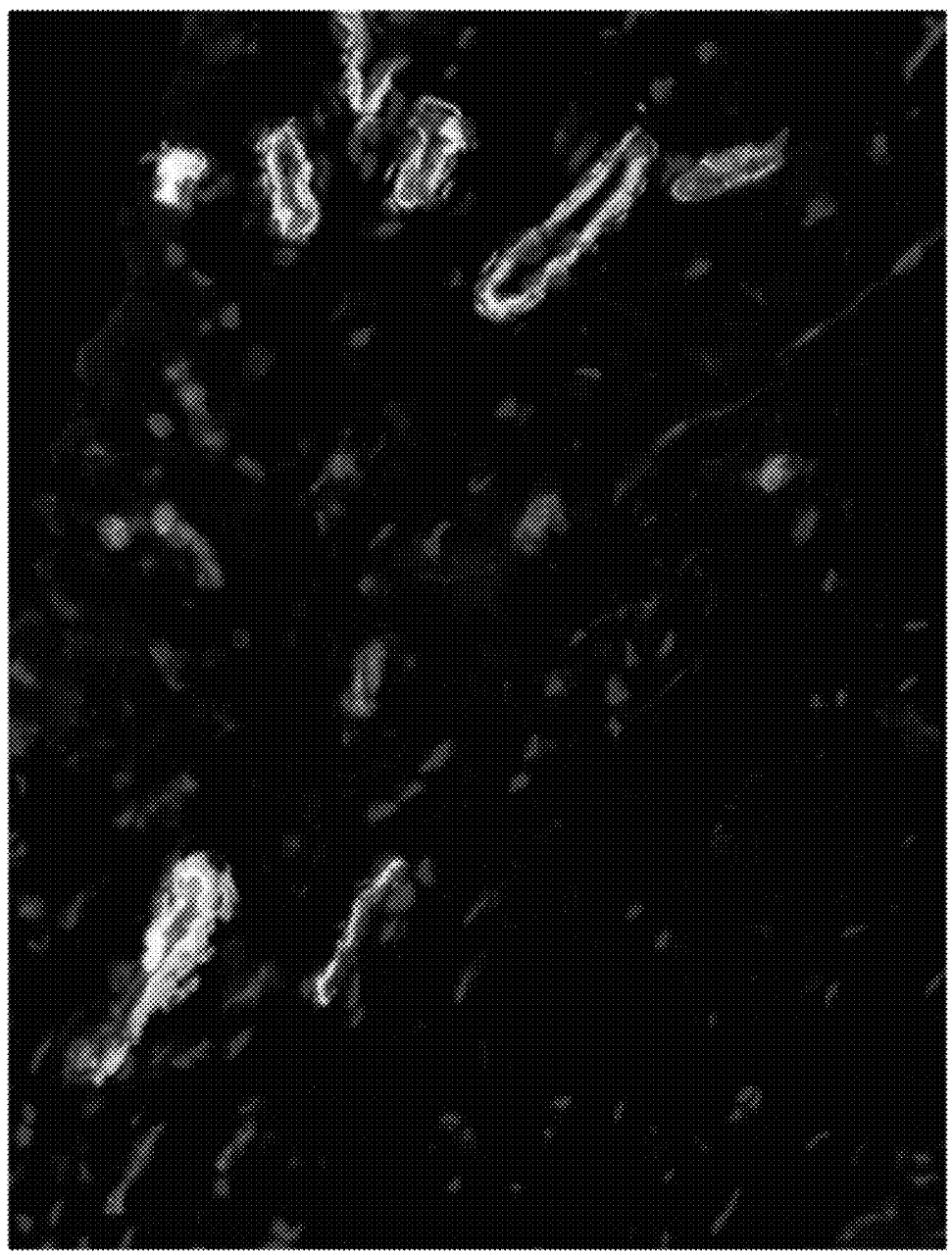
Figure 8C:
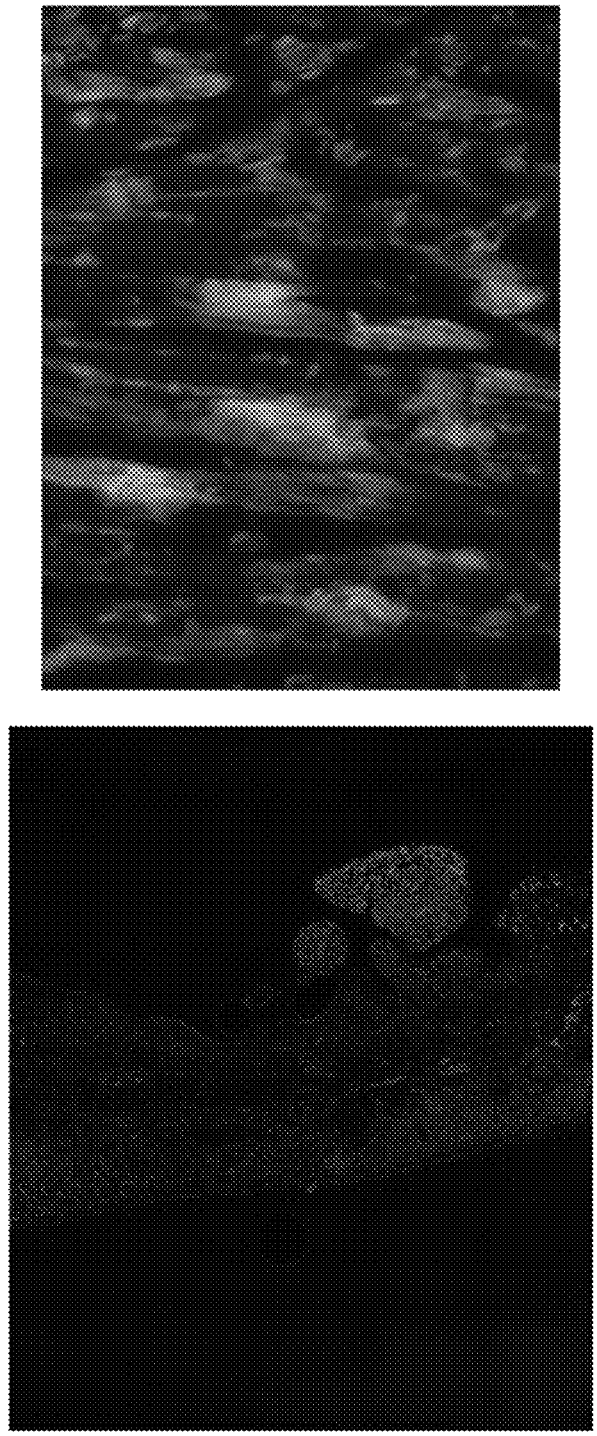
Figure 8D:
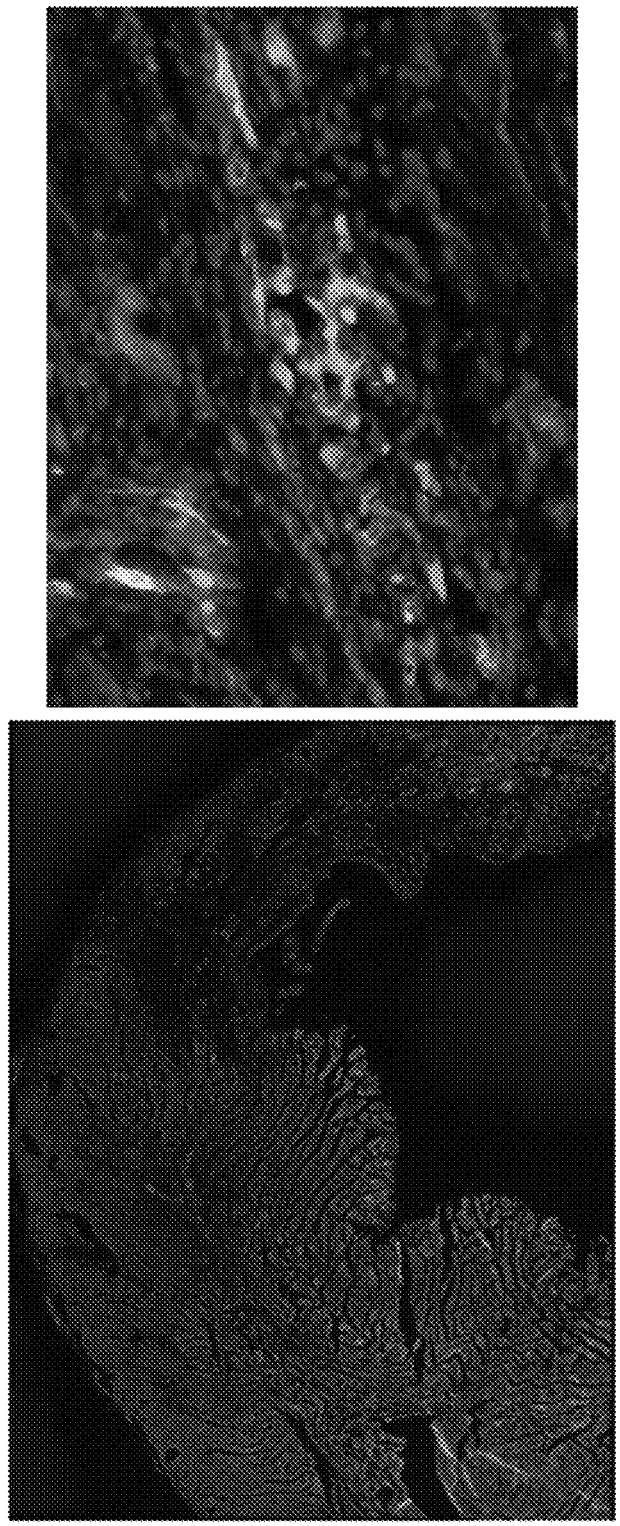

(7) Engraftment and APN Production of ADRCs Cell Cluster on Myocardial Infarction Area The ADRCs cell cluster transplanted on the left ventricular anterior wall of a myocardial infarction model rat was successfully engrafted on the scar area in the left ventricular anterior wall on day 28 after the transplantation (FIG. 8A), and demonstrated adiponectin positive at the transplanted site (FIG. 8B). This suggested that the successfully engrafted cell cluster secreted adiponectin persistently. In addition, in the groups, as the comparison targets, treated with the intramyocardial (FIG. 8C) and intracoronary (FIG. 8D) transplantation of ADRCs, engraftment success in the cardiomyocyte was also observed on day 3 after the transplantation.

Example 2

In order to analyze constituent cells of ADRCs, cell surface antigens were analyzed using flow cytometry (FACS). Fresh ADRCs extracted from adipose tissue by the method described in Example 1 were suspended in a FACS staining solution (a phosphate buffered saline supplemented with 5% fetal bovine serum). The analysis used mouse antibodies against CD11b, CD31, CD45, CD73, and CD90 as surface antigen markers, and the corresponding mouse IgG1 isotypes as negative markers. The cells were stained for 30 minutes at room temperature, washed and then analyzed using flow cytometry (BD FACS cant II instrument (BD Biosciences, San Jose, Calif.)).

As a result, the constituent cells of ADRC were mainly mesenchymal stem cells/mesenchymal progenitor cells (CD90+, CD31−, CD45−, and CD73+), endothelial cells (CD90+, CD31+, and CD45−), vascular smooth muscle (CD90−, CD31−, and CD45−), and hematopoietic cells (CD90+/−, CD31−, and CD45+). The approximate constituent ratio is as shown in Table 1. In particular, 6.5% of adipose tissue-derived mesenchymal stem cells were contained.

TABLE 1

| Cell Type | Constituent Ratio |
| --- | --- |
| Mesenchymal Stem Cells/Mesenchymal Progenitor Cells (CD90+, CD31−, CD45−, CD73+) | 6.5% |
| Vascular Smooth Muscle Cells (CD90−, CD31−, CD45−) | 13.2% |
| Vascular Endothelial Cells (CD90+, CD31−, CD45−) | 5.6% |
| Hematopoietic Cell (CD90+/−, CD31−, CD45+) | 26.5% |

INDUSTRIAL APPLICABILITY

As mentioned above, the transplant material of the present invention comprises a cell cluster in which isolated cells are caused to adhere to each other, and can be produced easily within a short period of time. Moreover, the transplant material secretes adiponectin, and has an excellent therapeutic effect of heart disease. Therefore, the present invention can greatly contribute to the development of transplant medical care mainly for heart disease.

The invention claimed is:

1. A method for improving cardiac function, said method comprising:
   treating isolated human adipose-derived regenerative cells with a PPARγ agonist,
   contacting the treated human adipose-derived regenerative cells with an adhesive agent for 5 minutes to 10 minutes before transplantation to form a transplant material comprising a cell cluster, and
   covering a cardiac surface of a subject in need thereof with said transplant material,
   wherein said isolated human adipose-derived regenerative cells comprise mesenchymal stem cells and mesenchymal progenitor cells,
   wherein said adhesive agent comprises fibrinogen and,
   wherein said isolated human adipose-derived regenerative cells in said cell cluster are autologous with respect to said subject.

2. The method according to claim 1, wherein the subject is in need of treatment for a disease selected from the group consisting of heart failure, ischemic heart disease, myocardial infarction, cardiomyopathy, myocarditis, hypertrophic cardiomyopathy, diastolic hypertrophic cardiomyopathy, and dilated cardiomyopathy.

* * * * *